US011680081B2

(12) United States Patent
Rodrigo et al.

(10) Patent No.: US 11,680,081 B2
(45) Date of Patent: Jun. 20, 2023

(54) METHOD FOR PREPARATION OF A SEPARATION MATRIX

(71) Applicant: Cytiva Bioprocess R&D AB, Uppsala (SE)

(72) Inventors: Gustav Rodrigo, Uppsala (SE); Mats Ander, Uppsala (SE); Ronnie Palmgren, Uppsala (SE); Tomas Bjorkman, Uppsala (SE)

(73) Assignee: CYTIVA BIOPROCESS R&D AB, Uppsala (SE)

( * ) Notice: Subject to any disclaimer, the term of this patent is extended or adjusted under 35 U.S.C. 154(b) by 265 days.

(21) Appl. No.: 16/955,119

(22) PCT Filed: Dec. 13, 2018

(86) PCT No.: PCT/EP2018/084702
§ 371 (c)(1),
(2) Date: Jun. 18, 2020

(87) PCT Pub. No.: WO2019/121296
PCT Pub. Date: Jun. 27, 2019

(65) Prior Publication Data
US 2021/0163529 A1 Jun. 3, 2021

(30) Foreign Application Priority Data
Dec. 20, 2017 (GB) ..................... 1721476

(51) Int. Cl.
| | | |
|---|---|---|
| *C07K 1/22* | (2006.01) | |
| *B01D 15/38* | (2006.01) | |
| *B01J 20/24* | (2006.01) | |
| *B01J 20/28* | (2006.01) | |
| *B01J 20/288* | (2006.01) | |
| *B01J 20/30* | (2006.01) | |
| *B01J 20/32* | (2006.01) | |
| *C07K 16/00* | (2006.01) | |

(52) U.S. Cl.
CPC ............ *C07K 1/22* (2013.01); *B01D 15/3809* (2013.01); *B01J 20/24* (2013.01); *B01J 20/288* (2013.01); *B01J 20/28016* (2013.01); *B01J 20/3071* (2013.01); *B01J 20/3212* (2013.01); *B01J 20/3217* (2013.01); *B01J 20/3274* (2013.01); *B01J 20/3295* (2013.01); *C07K 16/00* (2013.01); *B01J 2220/54* (2013.01)

(58) Field of Classification Search
CPC ...... C07K 1/22; C07K 16/00; B01D 15/3809; B01J 20/24; B01J 20/28016; B01J 20/288; B01J 20/3071; B01J 20/3212; B01J 20/3217; B01J 20/3274; B01J 20/3295; B01J 2220/54
USPC ....................................................... 252/184
See application file for complete search history.

(56) References Cited

U.S. PATENT DOCUMENTS

| 11,566,082 B2 | 1/2023 | Rodrigo |
| 2017/0327534 A1 | 11/2017 | Rodrigo et al. |

FOREIGN PATENT DOCUMENTS

| EP | 3050902 A1 | 8/2016 |
| EP | 3335789 A1 | 6/2018 |
| JP | 2000-500649 A | 1/2000 |
| JP | 2016-079149 A | 5/2016 |
| JP | 2016-079153 A | 5/2016 |
| JP | 2017-037070 A | 2/2017 |
| WO | 2015046473 A1 | 4/2015 |
| WO | 2017/194594 A1 | 11/2017 |
| WO | 2017194592 A1 | 11/2017 |
| WO | 2017194594 A1 | 11/2017 |

OTHER PUBLICATIONS

PCT International Search Report and Written Opinion for PCT Application No. PCT/EP2018/084702 dated Apr. 8, 2019 (11 pages).
Great Britain Search Report for GB Application No. 1721476.8 dated Jun. 21, 2018 (7 pages).
Altschul et al., "Basic Local Alignment Search Tool," J. Mol. Biol., 1990, 215:403-410.
Arshady, "Styrene Based Polymer Supports Developed by Suspension Polymerization," Chimica e L'Industria, 1998, 70(9):70-75.
Gel Filtration Principles and Methods, Pharmacia LKB Biotechnology, 1991, pp. 6-13.
Hermanson et al., "Immobilized Affinity Ligand Techniques," Academic Press, 1992, pp. 51-136 and 195-251.
Hjerten, "The Preparation of Agarose Spheres for Chromatography of Molecules and Particles," Biochim. Biophys. Acta, 1964, 79:393-398.
Sidorin et al., "IgG-Binding Proteins of Bacteria," Biochemistry, 2011, 76(3):295-308.
Office Action Issued in Japanese Patent Application No. 2020-534551, dated Dec. 5, 2022 with English Summary (13 Pages).

*Primary Examiner* — Edward M Johnson
(74) *Attorney, Agent, or Firm* — Eversheds Sutherland (US) LLP

(57) ABSTRACT

Methods that include providing and reacting a solid support and an alkali-stable ligand derived from an immunoglobulin-binding bacterial protein to form a separation matrix having covalently coupled alkali-stable ligands; and washing with a wash solution comprising at least 10 mM of an alkali metal hydroxide.

48 Claims, 3 Drawing Sheets
Specification includes a Sequence Listing.

METHOD FOR PREPARATION OF A SEPARATION MATRIX

CROSS REFERENCE TO RELATED APPLICATIONS

This application claims the priority benefit of PCT/EP2018/084702 filed on Dec. 13, 2018, which claims priority benefit of Great Britain Patent Application No. 1721476.8 filed on Dec. 20, 2017, the entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Jul. 31, 2020, is named 320948-US-6 (34428-0521) SL.txt and is 114,827 bytes in size.

TECHNICAL FIELD OF THE INVENTION

The present invention relates to manufacturing of affinity separation matrices and in particular to manufacturing of affinity separation matrices comprising covalently attached ligands derived from bacterial immunoglobulin-binding proteins such as *Staphylococcus* Protein A (SpA) *Peptostreptococcus* Protein L (PpL) or *Streptococcus* Protein G (SpG). The invention particularly relates to manufacturing of matrices comprising alkali-stable variants of these immunoglobulin-binding proteins.

BACKGROUND OF THE INVENTION

One of the most important classes of new pharmaceuticals is therapeutic monoclonal antibodies (mAbs). In the manufacturing of these, affinity chromatography on matrices comprising covalently coupled *Staphylococcus* Protein A (SpA) or variants of SpA is almost universally used as a first separation step to remove most of the contaminants originating from cell culture broths comprising the mAbs. The purity demands on the final mAb product are high and it is essential that any leakage of SpA ligand from the matrices is minimized, to avoid having to remove leaked ligands by subsequent chromatography steps. Such steps have been described in e.g. U.S. Pat. Nos. 6,121,428, 7,223,848, 7,847,071, US20080312425, U.S. Pat. Nos. 8,053,565 and 7,714,112, hereby incorporated by reference in their entireties. Methods of reducing the amounts of ligand leaking from the matrices during use are disclosed in U.S. Pat. Nos. 7,485,704, 7,589,183 and US20030148540, also hereby incorporated by reference in their entireties.

SpA is a member of the class of bacterial immunoglobulin-binding proteins (IBP), as reviewed by E V Sidorin and T F Soloveva in Biochemistry (Moscow), vol. 76, no. 3, p. 295-308 (2011). As discussed above, SpA is the most common IBP used in affinity chromatography of full antibodies, which is due to its highly selective binding to the Fc part of intact immunoglobulins. There is however also a strong trend of developing antibody fragments and other antibody constructs lacking the Fc part. In this case, IBPs, binding to other parts than the Fc part are used, most notably *Peptostreptococcus magnus* Protein L (PpL), which binds to the light chains of κ-type IgG and *Streptococcus* Protein G (SpG), which binds to the heavy chain of Fab fragments.

In the manufacturing of affinity separation matrices with IBP ligands such as SpA, PpL or SpG, solid supports, such as porous support particles, are typically activated to produce groups capable of reacting with the IBP ligands, and the activated support particles are then reacted with IBP ligands to achieve the desired covalent coupling. As a certain excess of ligand has to be applied, the matrix will however also comprise non-covalently bound ligands, which may be freely dissolved or be physically associated with the matrix. The free ligands are potentially toxic and to remove these non-covalently bound ligands to the extent needed for negligible or minimal leakage, extensive washing operations are needed, which add to the complexity and cost of the manufacturing process.

Accordingly, there is a need for an improved method of manufacturing affinity separation matrices with low leakage of IBP ligands such as SpA, PpL or SpG.

SUMMARY OF THE INVENTION

One aspect of the invention is to provide an efficient manufacturing method for a separation matrix with low leakage of IBP ligands such as SpA, PpL or SpG. This is achieved with a method comprising the steps of:

a) providing a solid support and an alkali-stable IBP, Protein A, Protein L or Protein G ligand;

b) reacting the alkali-stable IBP, Protein A, Protein L or Protein G ligand with the solid support to form a separation matrix having covalently coupled alkali-stable IBP, Protein A, Protein L or Protein G ligands; and c) washing the separation matrix having covalently coupled alkali-stable IBP, Protein A, Protein L or Protein G ligands with a wash solution comprising at least 10 mM, such as at least 25 mM, of an alkali metal hydroxide. The alkali metal hydroxide can e.g. be NaOH or KOH or any mixture thereof.

One advantage is that the alkali/NaOH/KOH wash in step c) efficiently removes any non-covalently bound ligands, such that only a limited number of wash steps are needed to lower the ligand leakage to acceptable levels. A further advantage is that any remaining reactive groups such as epoxide groups are inactivated by the alkali/NaOH/KOH wash.

Further suitable embodiments of the invention are described in the dependent claims.

DRAWINGS

DEFINITIONS

Figure 1:
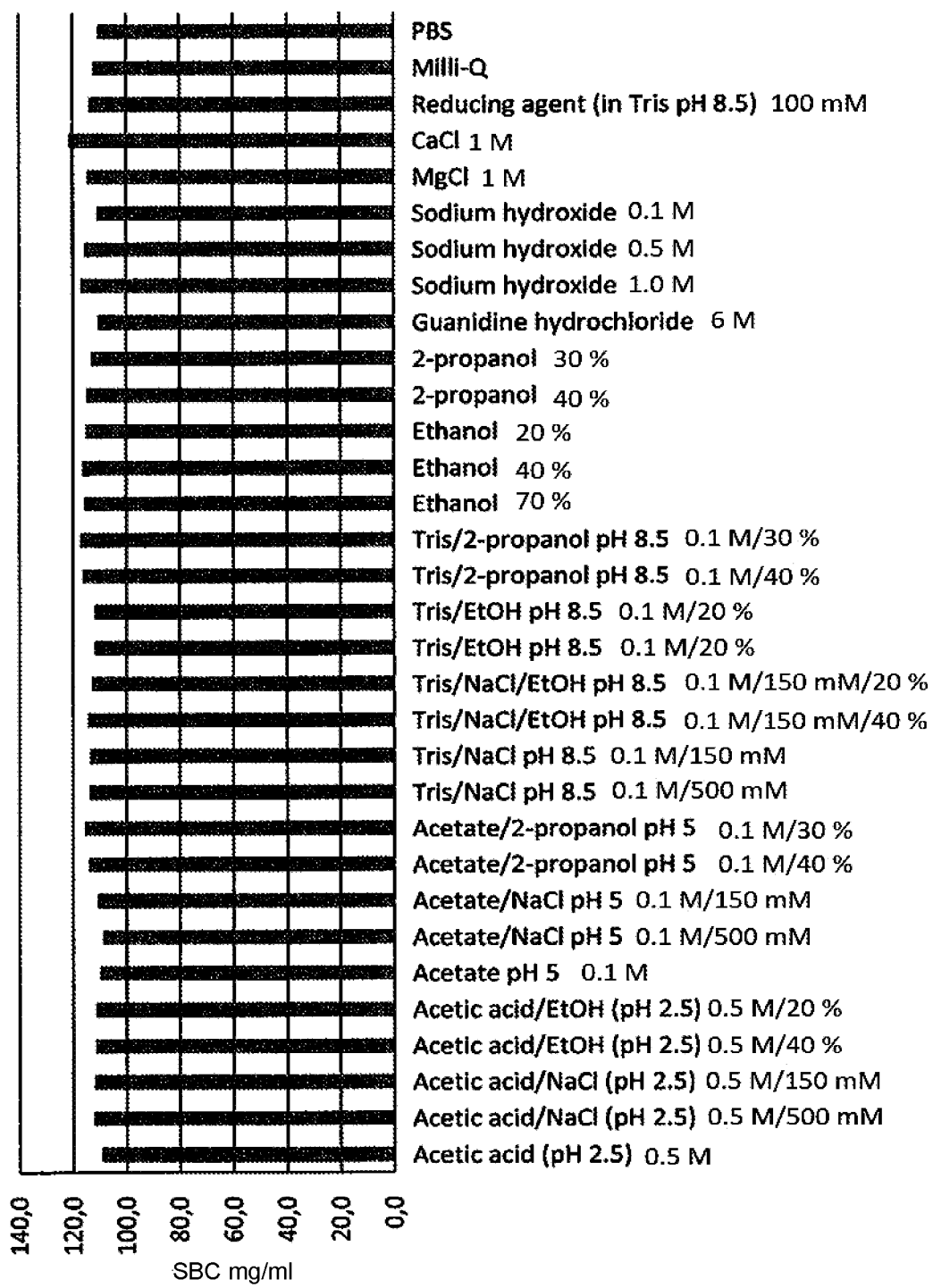
FIG. 1 shows the remaining static IgG-binding capacity of an alkali-stable Protein A separation matrix after 18 h incubation in different wash solutions.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "% identity" with respect to comparisons of amino acid sequences is determined by standard alignment algorithms such as, for example, Basic Local Alignment Tool (BLAST™) described in Altshul et al. (1990) J. Mol. Biol., 215: 403-410. A web-based software for this is freely available from the US National Library of Medicine at http://blast.ncbi.nlm.nih.gov/Blast.cgi?PROGRAM= blastp&PAGE TYPE=BlastSearch&LINK_LOC= blasthome. Here, the algorithm "blastp (protein-protein BLAST)" is used for alignment of a query sequence with a subject sequence and determining i.a. the % identity.

DETAILED DESCRIPTION OF EMBODIMENTS

In one aspect, the present invention discloses a method for preparation of a separation matrix, comprising the steps of a)-c). This method can also be described as a method of removing non-covalently bound Protein A, Protein L or Protein G ligand from the separation matrix, during or immediately after the preparation. As such it is also a method of preparing a separation matrix comprising covalently coupled alkali-stable Protein A, Protein L or Protein G ligands and being substantially free from non-covalently coupled Protein A, Protein L or Protein G ligands:

a) Providing a solid support and an alkali-stable Protein A, Protein L or Protein G ligand. The solid support may comprise a plurality of porous support particles, which may e.g. comprise a crosslinked polysaccharide, such as agar or agarose. The porous support particles can suitably be bead-shaped, e.g. with a sphericity of at least 0.9, where the sphericity is defined as the ratio of the surface area of a sphere with the same volume as the given particle to the surface area of the particle. The volume-weighted median diameter (d50,v) of the particles can e.g. be 10-200 micrometers, such as 20-150 micrometers. Further properties of porous support particles are discussed below. Alternatively, the solid support may comprise a porous membrane or porous monolith, e.g. a fibrous membrane, such as a non-woven nano fiber membrane. The nature of the alkali-stable Protein A, Protein L or Protein G ligand is also discussed further below. The ligand suitably comprises amino acid residues capable of chemical reaction with reactive groups on the solid support or porous support particles. Such amino acid residues can be lysines with a reactive amine, histidines with a reactive imidazole and/or cysteine with a reactive thiol.

b) Reacting the alkali-stable Protein A, Protein L or Protein G ligand with the solid support or porous support particles to form a separation matrix having covalently coupled alkali-stable Protein A, Protein L or Protein G ligands. Step b) may be preceded by a step a') of activating the solid support or porous support particles. This can e.g. involve the formation of aldehyde or epoxide groups on the support particles, e.g. by periodate oxidation of vicinal diols or by reaction with epichlorohydrin or a difunctional epoxide such as butanediol diglycidyl ether. Aldehyde groups can be used for coupling of amines on the ligands (e.g. lysine residues) by reductive amination, while epoxide groups can be used for coupling of nucleophilic groups, such as amines (e.g. lysine residues), imidazoles (histidines) or thiols (e.g. cysteine residues). If any epoxide groups remain after step b), they will be converted to non-reactive diols by the alkaline washing in step c). This obviates the need for applying any specific deactivation reagents such as thiols (typically thioglycerol or mercaptoethanol) or amines (e.g. ethanolamine) and the need to monitor any potential leakage of the deactivation agent from the final product. Activation and coupling methods are generally well known in the art and described e.g. in G T Hermanson, A K Mallia, P K Smith: Immobilized Affinity Ligand Techniques, Academic Press 1992, p. 51-136 and 195-251. Specific examples of activation and coupling methods that can be used with alkali-stable Protein A, Protein L or Protein G ligands in step b) are provided in e.g. US20170334954, U.S. Pat. Nos. 6,399,750, 8,114,611, 8,674,073, US2010221844 and U.S. Pat. No. 9,040,661, all of which are hereby incorporated by reference in their entireties. The ligand content of the separation matrix can suitably be at least 11 mg covalently bound ligand per mL separation matrix, such as at least 15 mg/mL, 11-20 mg/mL or 15-20 mg ligand per mL separation matrix. At high ligand contents, the risks for ligand leakage are higher and the efficiency demands on the wash method are increased.

c) Washing the separation matrix having covalently coupled alkali-stable Protein A, Protein L or Protein G ligands with a wash solution comprising at least 50 mM alkali hydroxide, such as NaOH or KOH. The wash solution may comprise 40 mM-1 M NaOH or KOH, 50 mM-1 M NaOH or KOH or 90 mM-1 M NaOH or KOH, such as 90 mM-0.5 M NaOH or KOH, or 90-200 mM NaOH or KOH or 40-200 mM NaOH or KOH. In case a mixture of NaOH and KOH is used, these values refer to the total concentration of alkali metal hydroxide. In the washing step, the separation matrix may e.g. be incubated with the wash solution during 2-30 min, such as 5-30 min or 5-15 min. After the incubation, the wash solution may be removed from particle matrices by filtration, although other methods such as sedimentation are also possible. In the latter case, enhanced sedimentation, e.g. by centrifugation (e.g. in a decanter centrifuge), is preferred to avoid slow gravity sedimentation steps. Filtration can be used both in small lab scale, where a filter plate, chromatography column etc. can be used, in intermediate lab scale with e.g. a glass filter funnel or Buchner funnel, and in large production scale, where e.g. an agitated Nutsch filter can be conveniently used. The temperature during step c) may e.g. be 2-40° C., such as 15-30° C. or 20-25° C. Step c) can suitably be repeated at least once, such as at least 5 times or 5-15 times. The washing may suitably be performed within 24 h after step b).

After step c), the method may further comprise a step d) of transferring the separation matrix to a storage solution. After this, the separation matrix may further be dispensed into transport containers for shipment to customers. After step c), the separation matrix is suitably substantially free from non-covalently bound Protein A, Protein L or Protein G ligands. This can be assessed with a ligand leakage test here described for Protein A (suitably performed at 22+/−2° C.), where the separation matrix is packed in a chromatography column, loaded with 16.65 mg polyclonal IgG (in a 0.020 M $NaH_2PO_4$, pH 7.0 loading buffer) per ml matrix and eluted with a 0.1 M glycine pH 3.0 elution buffer, to produce an eluate where all IgG-containing eluate fractions are pooled to form an IgG pool and the ligand content in the IgG pool is measured with a Protein A ELISA assay. If the ligand content is less than about 40 ng ligand per mg IgG in the pool, preferably less than about 30 ng, the separation matrix is considered to be substantially free from non-covalently bound Protein A ligands. Analogue methods can be used to determine the leakage of Protein L or Protein G ligands and the corresponding absence of non-covalently bound such ligands.

Porous Support Particles

The porous support particles can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo-or polyethylenoxy groups on their external and, if present, also on internal surfaces. The porous nature of the support particles means that their interior is accessible to the ligands and to immunoglobulins. In quantitative terms, the porous property can be expressed as a Kav or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. Kav is determined as the ratio $(V_e-V_0)/(V_t-V_0)$, where $V_e$ is the elution volume of a probe molecule (e.g. Dextran 110 kD), $V_0$ is the void volume of the column (e.g. the elution volume of a high Mw void marker, such as raw dextran) and $V_t$ is the total volume of the column. Kd can be determined as $(V_e-V_0)/V_t$, where $V_t$ is the elution volume of a salt (e.g. NaCl) able to access all the volume except the matrix volume (the volume occupied by the matrix polymer molecules). By definition, both Kd and Kav values always lie within the range 0-1. The Kav value can advantageously be 0.6-0.95, e.g. 0.7-0.90 or 0.6-0.8, as measured with dextran of Mw 110 kDa as a probe molecule. The Kd value as measured with dextran of Mw 110 kDa can suitably be 0.68-0.90, such as 0.68-0.85 or 0.70-0.85. An advantage of this is that the support has a large fraction of pores able to accommodate both the ligands and immunoglobulins binding to the ligands and to provide mass transport of the immunoglobulins to and from the binding sites. Alternatively, the support particles can be essentially non-porous, such as where the Kd value for dextran of Mw 110 kDa is below 0.1 or below 0.05. Such particles are primarily interesting for analytical separations and may have a volume-weighted median diameter (d50,v) of less than 10 micrometers, such as 1-10 or 1-5 micrometers.

In certain embodiments, the solid support or support particles comprise a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline washing.

In some embodiments, the support particles comprise agar or agarose. Such particles can easily be prepared according to standard methods, such as inverse suspension gelation (S Hjertén: Biochim Biophys Acta 79(2), 393-398 (1964). Alternatively, the support particles are commercially available products, such as crosslinked agarose beads sold under the name of SEPHAROSE™ FF (GE Healthcare). In an embodiment, which is especially advantageous for large-scale separations, the support particles have been adapted to increase their rigidity using the crosslinking methods described in U.S. Pat. Nos. 6,602,990 or 7,396,467, which are hereby incorporated by reference in their entireties, and hence rendering the particles more suitable for high flow rates.

In certain embodiments, the solid support or support particles, such as polymer, polysaccharide or agarose support particles, are crosslinked, such as with hydroxyalkyl ether crosslinks Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support particles and improves the chemical stability. Hydroxyalkyl ether crosslinks are alkali stable and do not cause any significant nonspecific adsorption.

Alternatively, the solid support or porous support particles can be based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as particles based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the support particles are magnetic. One example of such support particles is polysaccharide or synthetic polymer beads comprising e.g. magnetite particles, such that the beads can be used in magnetic batch separations.

Alkali-Stable Protein a Ligand

The alkali-stable Protein A ligand can be capable of withstanding incubation with 0.5 or 0.1 M NaOH for 100× 10 min at 22+/−2° C. with less than 45% reduction in binding capacity towards IgG, relative to the IgG binding capacity before incubation. The reduction in IgG binding capacity can suitable be less than 45%, such as less than 20% or less than 10%. This can suitably be measured by coupling the ligand to a surface plasmon resonance (SPR) chip, e.g. to Biacore CM5 sensor chips (GE Healthcare Bio-Sciences AB) as described in US20170334954, using e.g. NHS-coupling chemistry, and measuring the immunoglobulin-binding capacity of the chip in a Biacore instrument (GE Healthcare Bio-Sciences AB), typically using polyclonal human IgG, before and after incubation of the chip in 0.5 M NaOH for 100×10 min cycles. Alternatively, the alkali stability can be defined such that the separation matrix with the covalently bound ligands is capable of withstanding incubation with 0.5 M or 0.1 M NaOH for 100×15 min at 22+/−2° C. with less than 20% reduction in binding capacity towards IgG, relative to the IgG binding capacity before incubation. The reduction in IgG binding capacity can suitably be less than 15%, such as less than 10% or less than 5%. The assessment can be made by measuring the 10% breakthrough dynamic capacity (Qb10%) at 2.4 or 6 min residence time, as described in US20170334954.

The alkali-stable Protein A ligand can suitably comprise one or more mutated IgG-binding domains of SpA. The native SpA domains are the E-domain (SEQ ID NO. 1), the D-domain (SEQ ID NO. 2), the A-domain (SEQ ID NO. 3), the B-domain (SEQ ID NO. 4) and the C-domain (SEQ ID NO. 1). The mutations can involve the substitution of one or more asparagine residues by other amino acid residues, but other mutations are also possible. The structure of the alkali-stable Protein A ligand can typically be a protein L-(Domain-S)$_n$-T, where L is a 1-10 amino acid leader sequence including the N-terminus, Domain is the (mutated) IgG-binding domain, S is an optional 1-15 amino acid spacer sequence, n is 1-10, such as 1, 2, 3, 4, 5, 6, 7, 8, 9 or 10, e.g. 3-7 or 4-6, and T is a 0-10 amino acid tail sequence, including the C-terminus (if T has at least one amino acid residue). For end-point coupling, L or T may comprise a coupling moiety, e.g. a cysteine or a plurality of lysines or histidines. The C-terminus may e.g. be a cysteine.

Alkali-stable Protein A ligands can in principle be divided into two tiers, with different degrees of alkali stability. The first tier includes ligands capable of withstanding incubation in 0.5 M NaOH, as discussed above, and the second tier includes ligands capable of withstanding incubation in 0.1 M NaOH, as discussed above, but not 0.5 M NaOH. Both first and second tier ligands can be used in the methods of the invention, but the first tier ligands allow a more free choice of wash conditions. The first tier ligands includes ligands comprising the following Domain sequences: SEQ ID NO: 8-11, 17-23, 32, 34, 36-47, 49-50, 54-62, 65-69, 71, 136-138 and 142-147. The second tier ligands include ligands comprising the following Domain sequences: SEQ ID NO: 5, 7, 12-15, 24-31, 33, 35, 48, 51-53, 63-64, 70, 72-135 and 139-141. The ligands may e.g. comprise Domains having at least 80%, such as at least 90% or at least 95% identity to an amino acid sequence selected from the group consisting of SEQ ID NO 5 and 7-141. Alternatively they may e.g. comprise Domains having at least 80%, such as at least 90% or at least 95% identity to an amino acid sequence selected from the group consisting of SEQ ID NO 8-11, 17-23, 32, 34, 36-47, 49-50, 54-62, 65-69, 71 and 136-138. Suitably, all the Domains in the ligands comprise sequences as discussed above. Further, any L, S and/or T sequences can suitably be alkali stable, e.g. by not containing any asparagine residues. The Domain sequences are listed below, with indications about where information about their alkali stability is shown.

```
                                                                    SEQ ID NO 1
(SpA E domain)
AQQ NAFYQVLNMP NLNADQRNGF IQSLKDDPSQ SANVLGEAQK LNDSQAPK SEQ ID NO 2
(SpA D domain)
ADA QQNKFNKDQQ SAFYEILNMP NLNEEQRNGF IQSLKDDPSQ STNVLGEAKK

LNESQAPK

SEQ ID NO 3
(SpA A domain)
A DNNFNKEQQ NAFYEILNMP NLNEEQRNGF IQSLKDDPSQ SANLLAEAKK

LNESQAPK

SEQ ID NO 4
(SpA B domain)
ADNKFNKEQQ NAFYEILHLP NLNEEQRNGF IQSLKDDPSQ SANLLAEAKK

LNDAQAPK

SEQ ID NO 5
(SpA C domain)
ADNKFNKEQQ NAFYEILHLP NLTEEQRNGF IQSLKDDPSV SKEILAEAKK

LNDAQAPK

SEQ ID NO 6
(Protein Z) U.S. Pat. No. 7,834,158
VDNKFNKEQQ NAFYEILHLP NLNEEQRNAF IQSLKDDPSQ SANLLAEAKK

LNDAQAPK

SEQ ID NO 7
(Zvar) U.S. Pat. No. 7,834,158
VDAKFDKEQQ NAFYEILHLP NLTEEQRNAF IQSLKDDPSQ SANLLAEAKK

LNDAQAPK

SEQ ID NO 8
Zvar(Q9A, N11E, N43A) WO2017194594A1
VDAKFDKEAQ EAFYEILHLP NLTEEQRNAF IQSLKDDPSQ SAALLAEAKK

LNDAQAPK

SEQ ID NO 9
Zvar(Q9A, N11E, N28A, N43A) WO2017194594A1
VDAKFDKEAQ EAFYEILHLP NLTEEQRAAF IQSLKDDPSQ SAALLAEAKK

LNDAQAPK

SEQ ID NO 10
Zvar(Q9A, N11E, Q40V, A42K, N43E, L44I) WO2017194594A1
VDAKFDKEAQ EAFYEILHLP NLTEEQRNAF IQSLKDDPSV SKEILAEAKK

LNDAQAPK
```

-continued

Zvar(Q9A, N11E, Q40V, A42K, N43A, L44I) WO2017194594A1
SEQ ID NO 11
VDAKFDKEAQ EAFYEILHLP NLTEEQRNAF IQSLKDDPSV SKAI**LAEAKK

LNDAQAPK

Zvar(N11E, Q32A) WO2017194594A1
SEQ ID NO 12
VDAKFDKEQQ EAFYEILHLP NLTEEQRNAF IASLKDDPSQ SANLLAEAKK

LNDAQAPK

Zvar(N11E) WO2017194594A1
SEQ ID NO 13
VDAKFDKEQQ EAFYEILHLP NLTEEQRNAF IQSLKDDPSQ SANLLAEAKK

LNDAQAPK

Zvar(N11E, Q32E, Q40E) WO2017194594A1
SEQ ID NO 14
VDAKFDKEQQ EAFYEILHLP NLTEEQRNAF IESLKDDPSE SANLLAEAKK

LNDAQAPK

Zvar(N11E, Q32E, K50R) WO2017194594A1
SEQ ID NO 15
VDAKFDKEQQ EAFYEILHLP NLTEEQRNAF IESLKDDPSQ SANLLAEAKR

LNDAQAPK

Zvar(N11K) WO2017194594A1
SEQ ID NO 16
VDAKFDKEQQ KAFYEILHLP NLTEEQRNAF IQSLKDDPSQ SANLLAEAKK

LNDAQAPK

Zvar(N11K, H18K, S33K, D37E, A42R, N43A, L44I, K50R, L51Y)
WO2017194594A1
SEQ ID NO 17
VDAKFDKEQQ KAFYEILKLP NLTEEQRNAF IQKLKDEPSQ SRAILAEAKR

YNDAQAPK

Zvar(Q9A, N11E, N28A, Q40V, A42K, N43A, L44I) WO2017194594A1
SEQ ID NO 18
VDAKFDKEAQ EAFYEILHLP NLTEEQRAAF IQSLKDDPSV SKAILAEAKK

LNDAQAPK

Zvar(Q9A, N11K, H18K, S33K, D37E, A42R, N43A, L44I, K50R, L51Y)
WO2017194594A1
SEQ ID NO 19
VDAKFDKEAQ KAFYEILKLP NLTEEQRAAF IQKLKDEPSQ SRAILAEAKR

YNDAQAPK

Zvar(N11K, H18K, D37E, A42R, N43A, L44I) WO2017194594A1
SEQ ID NO 20
VDAKFDKEQQ KAFYEILKLP NLTEEQRNAF IQSLKDEPSQ SRAILAEAKK

LNDAQAPK

Zvar(Q9A, N11K, H18K, D37E, A42R, N43A, L44I) WO2017194594A1
SEQ ID NO 21
VDAKFDKEAQ KAFYEILKLP NLTEEQRNAF IQSLKDEPSQ SRAILAEAKK

LNDAQAPK

Zvar(Q9A, N11K, H18K, D37E, A42R, N43A, L44I, K50R)
WO2017194594A1
SEQ ID NO 22
VDAKFDKEAQ KAFYEILKLP NLTEEQRNAF IQSLKDEPSQ SRAILAEAKR

LNDAQAPK

Zvar(Q9A, N11K, H18K, D37E, A42R) WO2017194594A1
SEQ ID NO 23
VDAKFDKEAQ KAFYEILKLP NLTEEQRNAF IQSLKDEPSQ SRNLLAEAKK

LNDAQAPK

-continued

SEQ ID NO 24
Zvar(D37E) WO2016079034A1
VDAKFDKEQQ NAFYEILHLP NLTEEQRNAF IQSLKDEPSQ SANLLAEAKK

LNDAQAPK

SEQ ID NO 25
C(Q9A, N11E, E43A) WO2017194594A1
ADNKFNKEAQ EAFYEILHLP NLTEEQRNGF IQSLKDDPSV SKAILAEAKK

LNDAQAPK

SEQ ID NO 26
Zvar(N11Y) WO2017194594A1
VDAKFDKEQQ YAFYEILHLP NLTEEQRNAF IQSLKDDPSQ SANLLAEAKK

LNDAQAPK

SEQ ID NO 27
Zvar(N11T) WO2017194594A1
VDAKFDKEQQ TAFYEILHLP NLTEEQRNAF IQSLKDDPSQ SANLLAEAKK

LNDAQAPK

SEQ ID NO 28
Zvar(N11F) WO2017194594A1
VDAKFDKEQQ FAFYEILHLP NLTEEQRNAF IQSLKDDPSQ SANLLAEAKK

LNDAQAPK

SEQ ID NO 29
Zvar(N11L) WO2017194594A1
VDAKFDKEQQ LAFYEILHLP NLTEEQRNAF IQSLKDDPSQ SANLLAEAKK

LNDAQAPK

SEQ ID NO 30
Zvar(N11W) WO2017194594A1
VDAKFDKEQQ WAFYEILHLP NLTEEQRNAF IQSLKDDPSQ SANLLAEAKK

LNDAQAPK

SEQ ID NO 31
Zvar(N11I) WO2017194594A1
VDAKFDKEQQ IAFYEILHLP NLTEEQRNAF IQSLKDDPSQ SANLLAEAKK

LNDAQAPK

SEQ ID NO 32
Zvar(N11M) WO2017194594A1
VDAKFDKEQQ MAFYEILHLP NLTEEQRNAF IQSLKDDPSQ SANLLAEAKK

LNDAQAPK

SEQ ID NO 33
Zvar(N11V) WO2017194594A1
VDAKFDKEQQ VAFYEILHLP NLTEEQRNAF IQSLKDDPSQ SANLLAEAKK

LNDAQAPK

SEQ ID NO 34
Zvar(N11A) WO2017194594A1
VDAKFDKEQQ AAFYEILHLP NLTEEQRNAF IQSLKDDPSQ SANLLAEAKK

LNDAQAPK

SEQ ID NO 35
Zvar(N11H) WO2017194594A1
VDAKFDKEQQ HAFYEILHLP NLTEEQRNAF IQSLKDDPSQ SANLLAEAKK

LNDAQAPK

SEQ ID NO 36
Zvar(N11R) WO2017194594A1
VDAKFDKEQQ RAFYEILHLP NLTEEQRNAF IQSLKDDPSQ SANLLAEAKK

LNDAQAPK

-continued

Zvar(Q9A, N11E, D37E, Q40V, A42K, N43A, L44I) WO2017194594A1
VDAKFDKEAQ EAFYEILHLP NLTEEQRNAF IQSLKDEPSV SKAILAEAKK

LNDAQAPK

SEQ ID NO 37

Zvar(Q9A, N11E, D37E, Q40V, A42R, N43A, L44I) WO2017194594A1
VDAKFDKEAQ EAFYEILHLP NLTEEQRNAF IQSLKDEPSV SRAILAEAKK

LNDAQAPK

SEQ ID NO 38

Zvar(Q9A, N11E, A29G, Q40V, A42K, N43A, L44I) WO2017194594A1
VDAKFDKEAQ EAFYEILHLP NLTEEQRNGF IQSLKDDPSV SKAILAEAKK

LNDAQAPK

SEQ ID NO 39

Zvar(Q9A, N11E, A29S, Q40V, A42K, N43A, L44I) WO2017194594A1
VDAKFDKEAQ EAFYEILHLP NLTEEQRNSF IQSLKDDPSV SKAILAEAKK

LNDAQAPK

SEQ ID NO 40

Zvar(Q9A, N11E, A29Y, Q40V, A42K, N43A, L44I) WO2017194594A1
VDAKFDKEAQ EAFYEILHLP NLTEEQRNYF IQSLKDDPSV SKAILAEAKK

LNDAQAPK

SEQ ID NO 41

Zvar(Q9A, N11E, A29Q, Q40V, A42K, N43A, L44I) WO2017194594A1
VDAKFDKEAQ EAFYEILHLP NLTEEQRNQF IQSLKDDPSV SKAILAEAKK

LNDAQAPK

SEQ ID NO 42

Zvar(Q9A, N11E, A29T, Q40V, A42K, N43A, L44I) WO2017194594A1
VDAKFDKEAQ EAFYEILHLP NLTEEQRNTF IQSLKDDPSV SKAILAEAKK

LNDAQAPK

SEQ ID NO 43

Zvar(Q9A, N11E, A29N, Q40V, A42K, N43A, L44I) WO2017194594A1
VDAKFDKEAQ EAFYEILHLP NLTEEQRNNF IQSLKDDPSV SKAILAEAKK

LNDAQAPK

SEQ ID NO 44

Zvar(Q9A, N11E, A29F, Q40V, A42K, N43A, L44I) WO2017194594A1
VDAKFDKEAQ EAFYEILHLP NLTEEQRNFF IQSLKDDPSV SKAILAEAKK

LNDAQAPK

SEQ ID NO 45

Zvar(Q9A, N11E, A29L, Q40V, A42K, N43A, L44I) WO2017194594A1
VDAKFDKEAQ EAFYEILHLP NLTEEQRNLF IQSLKDDPSV SKAILAEAKK

LNDAQAPK

SEQ ID NO 46

Zvar(Q9A, N11E, A29W, Q40V, A42K, N43A, L44I) WO2017194594A1
VDAKFDKEAQ EAFYEILHLP NLTEEQRNWF IQSLKDDPSV SKAILAEAKK

LNDAQAPK

SEQ ID NO 47

Zvar(Q9A, N11E, A29I, Q40V, A42K, N43A, L44I) WO2017194594A1
VDAKFDKEAQ EAFYEILHLP NLTEEQRNIF IQSLKDDPSV SKAILAEAKK

LNDAQAPK

SEQ ID NO 48

Zvar(Q9A, N11E, A29M, Q40V, A42K, N43A, L44I) WO2017194594A1
VDAKFDKEAQ EAFYEILHLP NLTEEQRNMF IQSLKDDPSV SKAILAEAKK

LNDAQAPK

SEQ ID NO 49

```
Zvar(Q9A, N11E, A29V, Q40V, A42K, N43A, L44I) WO2017194594A1                    SEQ ID NO 50
VDAKFDKEAQ EAFYEILHLP NLTEEQRNVF IQSLKDDPSV SKAILAEAKK

LNDAQAPK

SEQ ID NO 51
Zvar(Q9A, N11E, A29D, Q40V, A42K, N43A, L44I) WO2017194594A1
VDAKFDKEAQ EAFYEILHLP NLTEEQRNDF IQSLKDDPSV SKAILAEAKK

LNDAQAPK

SEQ ID NO 52
Zvar(Q9A, N11E, A29E, Q40V, A42K, N43A, L44I) WO2017194594A1
VDAKFDKEAQ EAFYEILHLP NLTEEQRNEF IQSLKDDPSV SKAILAEAKK

LNDAQAPK

SEQ ID NO 53
Zvar(Q9A, N11E, A29H, Q40V, A42K, N43A, L44I) WO2017194594A1
VDAKFDKEAQ EAFYEILHLP NLTEEQRNHF IQSLKDDPSV SKAILAEAKK

LNDAQAPK

SEQ ID NO 54
Zvar(Q9A, N11E, A29R, Q40V, A42K, N43A, L44I) WO2017194594A1
VDAKFDKEAQ EAFYEILHLP NLTEEQRNRF IQSLKDDPSV SKAILAEAKK

LNDAQAPK

SEQ ID NO 55
Zvar(Q9A, N11E, A29K, Q40V, A42K, N43A, L44I) WO2017194594A1
VDAKFDKEAQ EAFYEILHLP NLTEEQRNKF IQSLKDDPSV SKAILAEAKK

LNDAQAPK

SEQ ID NO 56
Zvar(Q9A, N11E, Q40V, A42K, N43A, L44I, D53F) WO2017194594A1
VDAKFDKEAQ EAFYEILHLP NLTEEQRNAF IQSLKDDPSV SKAILAEAKK

LNFAQAPK

SEQ ID NO 57
Zvar(Q9A, N11E, Q40V, A42K, N43A, L44I, D53Y) WO2017194594A1
VDAKFDKEAQ EAFYEILHLP NLTEEQRNAF IQSLKDDPSV SKAILAEAKK

LNYAQAPK

SEQ ID NO 58
Zvar(Q9A, N11E, Q40V, A42K, N43A, L44I, D53W) WO2017194594A1
VDAKFDKEAQ EAFYEILHLP NLTEEQRNAF IQSLKDDPSV SKAILAEAKK

LNWAQAPK

SEQ ID NO 59
Zvar(Q9A, N11E, Q40V, A42K, N43A, L44I, D53K) WO2017194594A1
VDAKFDKEAQ EAFYEILHLP NLTEEQRNAF IQSLKDDPSV SKAILAEAKK

LNKAQAPK

SEQ ID NO 60
Zvar(Q9A, N11E, Q40V, A42K, N43A, L44I, D53R) WO2017194594A1
VDAKFDKEAQ EAFYEILHLP NLTEEQRNAF IQSLKDDPSV SKAILAEAKK

LNRAQAPK

SEQ ID NO 61
Zvar(Q9del, N11E, Q40V, A42K, N43A, L44I) WO2017194594A1
VDAKFDKE_Q EAFYEILHLP NLTEEQRNAF IQSLKDDPSV SKAILAEAKK

LNDAQAPK
```

Zvar(Q9A, N11E, Q40del, A42K, N43A, L44I) WO2017194594A1    SEQ ID NO 62
VDAKFDKEAQ EAFYEILHLP NLTEEQRNAF IQSLKDDPS_ SKAILAEAKK

LNDAQAPK

Zvar(Q9A, N11E, Q40V, A42del, N43A, L44I) WO2017194594A1    SEQ ID NO 63
VDAKFDKEAQ EAFYEILHLP NLTEEQRNAF IQSLKDDPSV S_AILAEAKK

LNDAQAPK

Zvar(Q9A, N11E, Q40V, A42K, N43del, L44I) WO2017194594A1    SEQ ID NO 64
VDAKFDKEAQ EAFYEILHLP NLTEEQRNAF IQSLKDDPSV SK_ILAEAKK

LNDAQAPK

Zvar(D2del, A3del, K4del, Q9A, N11E, Q40V, A42K, N43A, L44I)    SEQ ID NO 65
WO2017194594A1
V___FDKEAQ EAFYEILHLP NLTEEQRNAF IQSLKDDPSV SKAILAEAKK

LNDAQAPK

Zvar(V1del, D2del, Q9A, N11E, Q40V, A42K, N43A, L44I, K58del)    SEQ ID NO 66
WO2017194594A1
__AKFDKEAQ EAFYEILHLP NLTEEQRNAF IQSLKDDPSV SKAILAEAKK

LNDAQAP_

Zvar(K4del, F5del, D6del, K7del, E8del, Q9A, N11E, Q40V, A42K, N43A, L44I)    SEQ ID NO 67
WO2017194594A1
VDA_____AQ EAFYEILHLP NLTEEQRNAF IQSLKDDPSV SKAILAEAKK

LNDAQAPK

Zvar(Q9A, N11E, Q40V, A42K, N43A, L44I, A56del, P57del, K58del)    SEQ ID NO 68
WO2017194594A1
VDAKFDKEAQ EAFYEILHLP NLTEEQRNAF IQSLKDDPSV SKAILAEAKK

LNDAQ__

Zvar(V1del,, D2del, A3del, Q9A, N11E, Q40V, A42K, N43A, L44I)    SEQ ID NO 69
WO2017194594A1
___KFDKEAQ EAFYEILHLP NLTEEQRNAF IQSLKDDPSV SKAILAEAKK

LNDAQAPK

Zvar(V1del, D2del, A3del, K4del, F5del, D6del, K7del, E8del, Q9A, N11E, Q40V, A42K, N43A, L44I)    SEQ ID NO 70
WO2017194594A1
_____AQ EAFYEILHLP NLTEEQRNAF IQSLKDDPSV SKAILAEAKK

LNDAQAPK

Zvar(Q9A, N11E, Q40V, A42K, N43A, L44I, K58_insYEDG) WO2017194594A1    SEQ ID NO 71
VDAKFDKEAQ EAFYEILHLP NLTEEQRNAF IQSLKDDPSV SKAILAEAKK

LNDAQAPKYE DG

C(G29A) U.S. Pat. No. 8,329,860    SEQ ID NO 72
ADNKFNKEQQ NAFYEILHLP NLTEEQRNAF IQSLKDDPSV SKEILAEAKK

LNDAQAPK

C(N3del, K4del, F5del, N6del) U.S. Pat. No. 8,329,860    SEQ ID NO 73
AD____KEQQ NAFYEILHLP NLTEEQRNGF IQSLKDDPSV SKEILAEAKK

LNDAQAPK

```
C(N3del, K4del, F5del, N6del, G29A) U.S. Pat. No. 8,329,860                                            SEQ ID NO 74
AD____KEQQ NAFYEILHLP NLTEEQRNAF IQSLKDDPSV SKEILAEAKK

LNDAQAPK

C(A1del, D2del, N3del, K4del) U.S. Pat. No. 9,018,305                                                  SEQ ID NO 75
____FNKEQQ NAFYEILHLP NLTEEQRNGF IQSLKDDPSV SKEILAEAKK

LNDAQAPK

C(A1del, D2del, N3del) U.S. Pat. No. 9,018,305                                                         SEQ ID NO 76
___KFNKEQQ NAFYEILHLP NLTEEQRNGF IQSLKDDPSV SKEILAEAKK

LNDAQAPK

C(A1del, D2del, N3del, K4del, G29K) WO2013109302                                                       SEQ ID NO 77
____FNKEQQ NAFYEILHLP NLTEEQRNKF IQSLKDDPSV SKEILAEAKK

LNDAQAPK

C(A1del, D2del, N3del, G29K) WO2013109302                                                              SEQ ID NO 78
___KFNKEQQ NAFYEILHLP NLTEEQRNKF IQSLKDDPSV SKEILAEAKK

LNDAQAPK

C(A1V, G29A) U.S. Pat. No. 9,040,661                                                                   SEQ ID NO 79
VDNKFNKEQQ NAFYEILHLP NLTEEQRNAF IQSLKDDPSV SKEILAEAKK

LNDAQAPK

C(G29E) U.S. Pat. No. 9,403,883                                                                        SEQ ID NO 80
ADNKFNKEQQ NAFYEILHLP NLTEEQRNEF IQSLKDDPSV SKEILAEAKK

LNDAQAPK

C(G29R) U.S. Pat. No. 9,403,883                                                                        SEQ ID NO 81
ADNKFNKEQQ NAFYEILHLP NLTEEQRNRF IQSLKDDPSV SKEILAEAKK

LNDAQAPK

C(G29I) U.S. Pat. No. 9,403,883                                                                        SEQ ID NO 82
ADNKFNKEQQ NAFYEILHLP NLTEEQRNIF IQSLKDDPSV SKEILAEAKK

LNDAQAPK

C(G29L) U.S. Pat. No. 9,403,883                                                                        SEQ ID NO 83
ADNKFNKEQQ NAFYEILHLP NLTEEQRNLF IQSLKDDPSV SKEILAEAKK

LNDAQAPK

C(G29F) U.S. Pat. No. 9,403,883                                                                        SEQ ID NO 84
ADNKFNKEQQ NAFYEILHLP NLTEEQRNFF IQSLKDDPSV SKEILAEAKK

LNDAQAPK

C(G29Y) U.S. Pat. No. 9,403,883                                                                        SEQ ID NO 85
ADNKFNKEQQ NAFYEILHLP NLTEEQRNYF IQSLKDDPSV SKEILAEAKK

LNDAQAPK

C(G29M) U.S. Pat. No. 9,403,883                                                                        SEQ ID NO 86
ADNKFNKEQQ NAFYEILHLP NLTEEQRNMF IQSLKDDPSV SKEILAEAKK

LNDAQAPK
```

-continued

SEQ ID NO 87
C(G29W) U.S. Pat. No. 9,403,883
ADNKFNKEQQ NAFYEILHLP NLTEEQRNWF IQSLKDDPSV SKEILAEAKK

LNDAQAPK

SEQ ID NO 88
C(G29V) U.S. Pat. No. 9,403,883
ADNKFNKEQQ NAFYEILHLP NLTEEQRNVF IQSLKDDPSV SKEILAEAKK

LNDAQAPK

SEQ ID NO 89
C(G29T) U.S. Pat. No. 9,403,883
ADNKFNKEQQ NAFYEILHLP NLTEEQRNTF IQSLKDDPSV SKEILAEAKK

LNDAQAPK

SEQ ID NO 90
C(G29D) U.S. Pat. No. 9,403,883
ADNKFNKEQQ NAFYEILHLP NLTEEQRNDF IQSLKDDPSV SKEILAEAKK

LNDAQAPK

SEQ ID NO 91
C(G29H) U.S. Pat. No. 9,403,883
ADNKFNKEQQ NAFYEILHLP NLTEEQRNHF IQSLKDDPSV SKEILAEAKK

LNDAQAPK

SEQ ID NO 92
C(G29S) U.S. Pat. No. 9,403,883
ADNKFNKEQQ NAFYEILHLP NLTEEQRNSF IQSLKDDPSV SKEILAEAKK

LNDAQAPK

SEQ ID NO 93
C(G29K) WO2013109302
ADNKFNKEQQ NAFYEILHLP NLTEEQRNKF IQSLKDDPSV SKEILAEAKK

LNDAQAPK

SEQ ID NO 94
C(N3G, N6E, G29A, V40Q, K42T, E43N, I44V, A46G) US20160237124
ADGKFEKEQQ NAFYEILHLP NLTEEQRNAF IQSLKDDPSQ STNVLGEAKK

LNDAQAPK

SEQ ID NO 95
C(N3G, N6E, G29A, Q32K, L34I, K35R, V40Q, K42T, E43N, I44V, A46G)
US20160237124
ADGKFEKEQQ NAFYEILHLP NLTEEQRNAF IKSIRDDPSQ STNVLGEAKK

LNDAQAPK

SEQ ID NO 96
C(A1V, N3insF, G29A) WO2016152946
VDNFKFNKEQQ NAFYEILHLP NLTEEQRNAF IQSLKDDPSV SKEILAEAKK

LNDAQAPK

SEQ ID NO 97
C(A1V, N3insL, G29A) WO2016152946
VDNLKFNKEQQ NAFYEILHLP NLTEEQRNAF IQSLKDDPSV SKEILAEAKK

LNDAQAPK

SEQ ID NO 98
C(A1V, N3insI, G29A) WO2016152946
VDNIKFNKEQQ NAFYEILHLP NLTEEQRNAF IQSLKDDPSV SKEILAEAKK

LNDAQAPK

SEQ ID NO 99
C(A1V, N3insP, G29A) WO2016152946
VDNPKFNKEQQ NAFYEILHLP NLTEEQRNAF IQSLKDDPSV SKEILAEAKK

LNDAQAPK

```
                                                           SEQ ID NO 100
C(A1V, N3insQ, G29A) WO2016152946

```
                                                         SEQ ID NO 113
Z(N23S) WO2012083425
VDNKFNKEQQ NAFYEILHLP NLSEEQRNAF IQSLKDDPSQ SANLLAEAKK

LNDAQAPK

SEQ ID NO 114
Z(N3H, N23S) WO2012083425
VDHKFNKEQQ NAFYEILHLP NLSEEQRNAF IQSLKDDPSQ SANLLAEAKK

LNDAQAPK

SEQ ID NO 115
Z(N3H, N23T) WO2012083425
VDHKFNKEQQ NAFYEILHLP NLTEEQRNAF IQSLKDDPSQ SANLLAEAKK

LNDAQAPK

SEQ ID NO 116
Z(N3H, N6D, N23S) WO2012083425
VDHKFDKEQQ NAFYEILHLP NLSEEQRNAF IQSLKDDPSQ SANLLAEAKK

LNDAQAPK

SEQ ID NO 117
C(G29A, P57del) EP1992692A1
ADNKFNKEQQ NAFYEILHLP NLTEEQRNAF IQSLKDDPSV SKEILAEAKK

LNDAQA_K

SEQ ID NO 118
Z(N3D, N6L, L19del, N23T) CN105481954A
VDDKFLKEQQ NAFYEILH_P NLTEEQRNAF IQSLKDDPSQ SANLLAEAKK

LNDAQAPK

SEQ ID NO 119
Z(N3A, N6D, Q9A, N23T) US20160159855
VDAKFDKEAQ NAFYEILHLP NLTEEQRNAF IQSLKDDPSQ SANLLAEAKK

LNDAQAPK

SEQ ID NO 120
Z(N3A, N6D, Q9A, E15K, N23T) US20160159855
VDAKFDKEAQ NAFYKILHLP NLTEEQRNAF IQSLKDDPSQ SANLLAEAKK

LNDAQAPK

SEQ ID NO 121
Z(N3A, N6D, Q9A, N23T, E47T) US20160159855
VDAKFDKEAQ NAFYEILHLP NLTEEQRNAF IQSLKDDPSQ SANLLATAKK

LNDAQAPK

SEQ ID NO 122
Z(N3A, N6D, Q9A, N23T, D36T) US20160159855
VDAKFDKEAQ NAFYEILHLP NLTEEQRNAF IQSLKTDPSQ SANLLAEAKK

LNDAQAPK

SEQ ID NO 123
Z(N3A, N6D, Q9A, N23T, D36A) US20160159855
VDAKFDKEAQ NAFYEILHLP NLTEEQRNAF IQSLKADPSQ SANLLAEAKK

LNDAQAPK

SEQ ID NO 124
Z(N3A, N6D, Q9T, N23T, D36T) US20160159855
VDAKFDKETQ NAFYEILHLP NLTEEQRNAF IQSLKTDPSQ SANLLAEAKK

LNDAQAPK

SEQ ID NO 125
Z(N3A, N6D, Q9A, N23T, Q26A, D36A, E47A) US20160159855
VDAKFDKEAQ NAFYEILHLP NLTEEARNAF IQSLKADPSQ SANLLAAAKK

LNDAQAPK
```

Z(N3A, N6D, Q9A, N23T, E47T, K49E, N525) US20160159855
VDAKFDKEAQ NAFYEILHLP NLTEEQRNAF IQSLKDDPSQ SANLLATAEK

LSDAQAPK

SEQ ID NO 126

Z(N3A, N6D, Q9T, N23T, E47T) US20160159855
VDAKFDKETQ NAFYEILHLP NLTEEQRNAF IQSLKDDPSQ SANLLATAKK

LNDAQAPK

SEQ ID NO 127

Z(N3A, N6D, Q9W, N23T) Ser. No. 14/961,164
VDAKFDKEWQ NAFYEILHLP NLTEEQRNAF IQSLKDDPSQ SANLLAEAKK

LNDAQAPK

SEQ ID NO 128

Z(N3A, N6D, Q9L, N23T) Ser. No. 14/961,164
VDAKFDKELQ NAFYEILHLP NLTEEQRNAF IQSLKDDPSQ SANLLAEAKK

LNDAQAPK

SEQ ID NO 129

Z(N3A, N6D, Q9E, N23T) Ser. No. 14/961,164
VDAKFDKEEQ NAFYEILHLP NLTEEQRNAF IQSLKDDPSQ SANLLAEAKK

LNDAQAPK

SEQ ID NO 130

Z(N3A, N6D, Q9K, N23T) Ser. No. 14/961,164
VDAKFDKEKQ NAFYEILHLP NLTEEQRNAF IQSLKDDPSQ SANLLAEAKK

LNDAQAPK

SEQ ID NO 131

Z(N3A, N6D, Q9V, N23T) Ser. No. 14/961,164
VDAKFDKEVQ NAFYEILHLP NLTEEQRNAF IQSLKDDPSQ SANLLAEAKK

LNDAQAPK

SEQ ID NO 132

Zvar(A42R) WO2016079034A1
VDAKFDKEQQ NAFYEILHLP NLTEEQRNAF IQSLKDDPSQ SRNLLAEAKK

LNDAQAPK

SEQ ID NO 133

Zvar(S33K, D37E, A42R, N43A, L44I, K50R, L51Y) WO2016079034A1
VDAKFDKEQQ NAFYEILHLP NLTEEQRNAF IQKLKDEPSQ SRAILAEAKR

YNDAQAPK

SEQ ID NO 134

Zvar(H18K, S33K, D37E, A42R, N43A, L44I, K50R, L51Y) WO2016079034A1
VDAKFDKEQQ NAFYEILKLP NLTEEQRNAF IQKLKDEPSQ SRAILAEAKR

YNDAQAPK

SEQ ID NO 135

Zvar(N11K, H18K, S33K, D37E, A42R, N43A, L44I, K50R, L51Y)
WO2016079034A1
VDAKFDKEQQ KAFYEILKLP NLTEEQRNAF IQKLKDEPSQ SRAILAEAKR

YNDAQAPK

SEQ ID NO 136

Zvar(Q9A, N11K, H18K, S33K, D37E, A42R, N43A, L44I, K50R, L51Y)
WO2016079034A1
VDAKFDKEAQ KAFYEILKLP NLTEEQRNAF IQKLKDEPSQ SRAILAEAKR

YNDAQAPK

SEQ ID NO 137

Zvar(N11K, H18K, D37E, A42R, N43A, L44I) WO2016079034A1
VDAKFDKEQQ KAFYEILKLP NLTEEQRNAF IQSLKDEPSQ SRAILAEAKK

LNDAQAPK

SEQ ID NO 138

-continued

Z(N23T) U.S. Pat. No. 7,834,158
VDNKFNKEQQ NAFYEILHLP NLTEEQRNAF IQSLKDDPSQ SANLLAEAKK

LNDAQAPK

Z(N3A, N23T) U.S. Pat. No. 7,834,158
VDNKFNKEQQ NAFYEILHLP NLTEEQRNAA IQSLKDDPSQ SANLLAEAKK

LNDAQAPK

Z(K4G, N23T) U.S. Pat. No. 7,834,158
VDNGFNKEQQ NAFYEILHLP NLTEEQRNAA IQSLKDDPSQ SANLLAEAKK

LNDAQAPK

WO2018029158
IAAQHDKEQQ AAFYEILHLP NLTEDQRNAF IQSLRDDPSV SLEILGEAKK LNDAQAPK

WO2018029158
IAAQHDKDQQ AAFYEILHLP NLTEEQRNAF IQSLRDDPSV SLEILAEAKK LNDAQAPK

WO2018029158
IAAQHDKEHQ AAFYEILHLP NLTEDQRNAF IQSLRDDPSV SLEILGEAKK LNDAQAPK

WO2018029158
IAAQHDKDHQ AAFYEILHLP NLTEEQRNAF IQSLRDDPSV SLEILAEAKK LNDAQAPK

WO2018029158
IAAQHDKEQQ AAFYEILHLP NLTEDQRNAF IQSLRHDPSV SLEILGEAKK LNDAQAPK

WO2018029158
IAAQHDKDQQ AAFYEILHLP NLTEEQRNAF IQSLRHDPSV SLEILAEAKK LNDAQAPK

SEQ ID NO 139

SEQ ID NO 140

SEQ ID NO 141

SEQ ID NO 143

SEQ ID NO 144

SEQ ID NO 145

SEQ ID NO 146

SEQ ID NO 147

SEQ ID NO 148

Alkali-Stable Protein L Ligand

The alkali-stable Protein L ligand can suitably comprise one or more mutated IgG-binding domains of PpL. The native PpL domains are Domain B1 (SEQ ID NO. 149), Domain B2 (SEQ ID NO. 150), Domain B3 (SEQ ID NO. 151), Domain B4 (SEQ ID NO. 152), Domain B5 (SEQ ID NO. 153), Domain C1 (SEQ ID NO 168), Domain C2 (SEQ ID NO 169), Domain C3 (SEQ ID NO 170), Domain C4 (SEQ ID NO 171) and Domain Dl (SEQ ID NO 172). The mutations can involve the substitution of one or more asparagine residues by other amino acid residues, but other mutations are also possible. The structure of the alkali-stable Protein L ligand can typically be a protein L'-(Domain'-S')$_n$-T', where L' is a 1-10 amino acid leader sequence including the N-terminus, Domain' is the (mutated) IgG-binding domain, S' is an optional 1-15 amino acid spacer sequence, n is 1-10, such as 1, 2, 3, 4, 5, 6, 7, 8, 9 or 10, e.g. 3-7 or 4-6, and T' is a 0-10 amino acid tail sequence, including the C-terminus (if T' has at least one amino acid residue).

SEQ ID NO 149
Protein L Domain B1 WO2016096643A1
SEEEVTIKAN LIFANGSTQT AEFKGTFEKA TSEAYAYADT

LKKDNGEYTV DVADKGYTLN IKFAGKEKTP EE

SEQ ID NO 150
Protein L Domain B2 WO2016096643A1
PKEEVTIKAN LIYADGKTQT AEFKGTFEEA TAEAYRYADA

LKKDNGEYTV DVADKGYTLN IKFAGKEKTP EE

SEQ ID NO 151
Protein L Domain B3 WO2016096643A1
PKEEVTIKAN LIYADGKTQT AEFKGTFEEA TAEAYRYADL

LAKENGKYTV DVADKGYTLN IKFAGKEKTP EE

SEQ ID NO 152
Protein L Domain B4 WO2016096643A1
PKEEVTIKAN LIYADGKTQT AEFKGTFAEA TAEAYRYADL

LAKENGKYTA DLEDGGYTIN IRFAGKKVDE KPE

SEQ ID NO 153
Protein L Domain B5 WO2016096643A1
EKEQVTIKEN IYFEDGTVQT ATFKGTFAEA TAEAYRYADL

LSKEHGKYTA DLEDGGYTIN IRFAG

SEQ ID NO 168
Protein L Domain C1
PEEEVTIKAN LIFADGSTQN AEFKGTFAKA VSDAYAYADA

LKKDNGEYTV DVADKGLTLN IKFAGKKEKP EE

SEQ ID NO 169
Protein L Domain C2
PKEEVTIKVN LIFADGKTQT AEFKGTFEEA TAKAYAYADL

LAKENGEYTA DLEDGGNTIN IKFAGKETPETP EE

```
                              SEQ ID NO 170
Protein L Domain C3
PKEEVTIKVN LIFADGKIQT AEFKGTFEEA TAKAYAYANL

LAKENGEYTA DLEDGGNTIN IKFAGKETPETP EE

SEQ ID NO 171
Protein L Domain C4
PKEEVTIKVN LIFADGKTQT AEFKGTFEEA TAEAYRYADL

LAKVNGEYTA DLEDGGYTIN IKFAGKEQPGEN PG

SEQ ID NO 172
Protein L Domain D1
PKEEVTIKAN LIFADGKTQT AEFKGTFEEA TAEAYRYADL

LAKVNGEYTA DLEDGGYTIN IKFAGKEQPGEN
```

The alkali-stable Protein L ligand can be capable of withstanding incubation with 0.1 M NaOH for 100×10 min at 22+/−2° C. with less than 45% reduction in binding capacity towards IgG, relative to the IgG binding capacity before incubation. This can suitably be measured by coupling the ligand to a surface plasmon resonance (SPR) chip, e.g. to Biacore CM5 sensor chips (GE Healthcare Bio-Sciences AB) as described in US20170334954, using e.g. NHS-coupling chemistry, and measuring the immunoglobulin-binding capacity of the chip in a Biacore instrument (GE Healthcare Bio-Sciences AB), typically using polyclonal human IgG, before and after incubation of the chip in 0.5 M NaOH for 100×10 min cycles. Alternatively, the alkali stability can be defined such that the separation matrix with the covalently bound ligands is capable of withstanding incubation with 0.5 M or 0.1 M NaOH for 100×15 min at 22+/−2° C. with less than 20% reduction in binding capacity towards IgG, relative to the IgG binding capacity before incubation. The reduction in IgG binding capacity can suitably be less than 15%, such as less than 10% or less than 5%. The assessment can be made by measuring the 10% breakthrough dynamic capacity (Qb10%) at 2.4 or 6 min residence time, as described in US20170334954.

Alkali-stable Protein L ligands as discussed above include monomeric and multimeric L'-(Domain'-S')$_n$-T' constructs of the following mutated domains, as described in WO2016096643A1, US20180305414 and WO2017191748A1, which are hereby incorporated by reference in their entireties.

```
                              SEQ ID NO 154
Protein L Domain B3(N10Q, N45A) WO2016096643A1
PKEEVTIKAQ LIYADGKTQT AEFKGTFEEA TAEAYRYADL

LAKEAGKYTV DVADKGYTLN IKFAGKEKTPEE

SEQ ID NO 155
Protein L Domain B3(N45A, N60Q) WO2016096643A1
PKEEVTIKAN LIYADGKTQT AEFKGTFEEA TAEAYRYADL

LAKEAGKYTV DVADKGYTLQ IKFAGKEKTPEE

SEQ ID NO 156
Protein L Domain B3(N10Q, N45A, N60Q)
WO2016096643A1
PKEEVTIKAQ LIYADGKTQT AEFKGTFEEA TAEAYRYADL

LAKEAGKYTV DVADKGYTLQ IKFAGKEKTPEE

SEQ ID NO 157
US20180305414
ETPEE PREEVTIRVN LIFADGRIQT AEFRGTFEEA TAKAYAYANL

LAKENGEYTA DLEDGGNTIN IKFAG

SEQ ID NO 158
WO2017191748
VTIKAN LIFANGSTQT AEFKGTFEKA TSEAYAYADT LKKDHGEYTV

DVADKGYTLN IKFA
```

Alkali-Stable Protein G Ligand

The alkali-stable Protein G ligand can suitably comprise one or more mutated IgG-binding domains of SpG. The mutations can involve the substitution of one or more asparagine residues by other amino acid residues, but other mutations are also possible. The structure of the alkali-stable Protein G ligand can typically be a protein L"-(Domain"-S")$_n$-T", where L" is a 1-10 amino acid leader sequence including the N-terminus, Domain" is the (mutated) IgG-binding domain, S" is an optional 1-15 amino acid spacer sequence, n is 1-10, such as 1, 2, 3, 4, 5, 6, 7, 8, 9 or 10, e.g. 3-7 or 4-6, and T" is a 0-10 amino acid tail sequence, including the C-terminus (if T" has at least one amino acid residue).

Alkali-stable Protein G ligands as discussed above include monomeric and multimeric L"-(Domain"-S")$_n$-T" constructs of the following mutated domains, as described in WO2018180204A1 and WO2018180205A1, which are hereby incorporated by reference in their entireties.

```
                              SEQ ID NO 159
WO2018180204 SEQ 1(N8D)
TTYKLILDGK TLKGETTTEA VDAATAEKVF KQYANDNGVD

GEWTYDDATK TFTVTE

SEQ ID NO 160
WO2018180204 SEQ 1(N8L)
TTYKLILLGK TLKGETTTEA VDAATAEKVF KQYANDNGVD

GEWTYDDATK TFTVTE

SEQ ID NO 161
WO2018180204 SEQ 4(N8I)
TTYKLILIGK TLTGYTTTIA VDAATAEKVL KQFANDNGVD

GEWTYDDATK TFTVTE

SEQ ID NO 162
WO2018180204 SEQ 4(N8K)
TTYKLILKGK TLTGYTTTIA VDAATAEKVL KQFANDNGVD

GEWTYDDATK TFTVTE

SEQ ID NO 163
WO2018180204 SEQ 4(N8L)
TTYKLILIGK TLTGYTTTIA VDAATAEKVL KQFANDNGVD

GEWTYDDATK TFTVTE

SEQ ID NO 164
WO2018180205 SEQ 3
TTYKLIVKGN TFSGETTTKA VDAETAEKAF KQYATANNVD

GEWSYDDATK TFTVTE

SEQ ID NO 165
WO2018180205 SEQ 4
TTYKLIVKGN TFSGETTTKA IDAATAEKEF KQYATANGVD

GEWSYDDATK TFTVTE
```

-continued

SEQ ID NO 166
WO2018180205 SEQ 11
TTYKLIVKGN TLTGYTTTIA VDAETAEKAL KQFANENGVY

GEWSYDDATK TFTVTE

SEQ ID NO 167
WO2018180205 SEQ 13
TTYRLVIKGV TLTGYTATIA VDAATAEQTL RQFANDNGIT

GEWAYDTATK TFTVTE

EXAMPLES

Prototype Matrix

Roughly 130 mL of an alkali stable Protein A matrix prototype was prepared by coupling of a hexameric highly alkali-stable ligand having the structure L-(Domain)$_6$-T, with L=AQGT (SEQ ID NO 142), Domain=SEQ ID NO 11 and T=a C-terminal cysteine, to highly crosslinked agarose beads. The beads were epoxy activated with epichlorohydrin before the coupling and the coupling was performed as described in U.S. Pat. No. 6,399,750. The ligand content after coupling was 18 mg/ml matrix After immobilization, the gel was washed twice with one gel volume of distilled water.

Activation

The porous support particles used were rigid cross-linked agarose beads of 62 micrometers (volume-weighted, d50V) median diameter, prepared according to the methods of U.S. Pat. No. 6,602,990, hereby incorporated by reference in its entirety, and with a pore size corresponding to an inverse gel filtration chromatography Kav value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750, hereby incorporated by reference in its entirety. All buffers used in the experiments had been degassed by nitrogen gas for at least 5-10 min.

Example 1—Effect of Different Wash Solutions on the IgG-Binding Capacity of an Affinity Separation Matrix A 10% gel slurry was prepared from 10 ml filter cake of the prototype matrix and adding 90.0 mL of 20% ethanol (90×0.97=87.3 g) (density of 20% ethanol is 0.97 g/mL). The slurry was then dispensed into a 96 well filter plate (GE Healthcare) with a Gilson robot, 200 µL slurry/well (20 µL gel/well). The plate was then drained with vacuum. The bottom of the filter plate was sealed and the solutions for the compatibility study were then pipetted into the filter plate, 200 µL/well. The plate was then stored in room temperature (22+/−2° C.) overnight for 18 h. The solutions were removed by using vacuum and the wells were washed approximately 10×200 µL with PBS buffer, with the last draining made by centrifugation 500 g for 1 min.

After exposure to these chemicals, static binding capacity was tested as follows. An IgG sample solution was prepared by diluting Gammanorm (Octapharma, polyclonal human IgG) 10× in PBS buffer. After wash/equilibration in PBS buffer, 250 µL sample/well was loaded and the plate was incubated on a shaker for 60 minutes. The wells were emptied with centrifugation into a UV plate and the amount of unbound IgG sample was detected as the 280 nm absorbances using a UV-reader after dilution 1:1 to ensure that the absorbances were within the linear range of the reader. The static binding capacities were calculated and divided by the static IgG capacity of the prototype before incubation.

The data are presented in FIG. 1, showing that none of the tested solutions, including 1 M NaOH, had any negative effect on the static IgG binding capacity of the prototype.

Example 2—Effect of Different Wash Solutions on the Removal of Unbound Ligands from an Affinity Separation Matrix A 10% gel slurry (in water) of the prototype matrix was prepared as above. into a 96 well filter plate (GE Healthcare) with a Gilson robot, 200 µL slurry/well (20 µL gel/well). The plate was then drained with vacuum. The bottom of the filter plate was sealed and the solutions for the wash efficiency study were then pipetted into the filter plate, 200 µL/well. The plate was then stored in room temperature (22+/−2° C.) 1 hour with shaking at 1200 rpm. The solutions were removed by using centrifugation, 500 g, for 1 min and the plate was again prepared with the solutions for the wash efficiency study as above. The eluted solutions were tested by LC-MS (Aquity UPLC system from Water with a Zorbax 300SB-C8 2.1×50 mm column and a Xevo G2 Q-TOF MS from Waters) to determine the ligand concentration as the total ion current (TIC) and a calibration curve prepared with free ligand in solution. The details for the LC-MS method were:

Buffer A: 0.1% Formic acid and 0.05% trifluoroacetic acid (TFA) in MilliQ™ water Buffer B: 0.1% Formic acid and 0.05% TFA in 80:20 Acetonitrile: 2-propanol The column was kept at 60° C. A volume of 10-50 µL of sample was injected depending on the concentration of samples and MS data was collected in Full MS Survey mode as given in the MS method.

MS Method

Time: 0-12 min

Polarity: Positive

Analyzer mode: Resolution m/z range: 50-4000

Scan time: 1 sec
Collision energy: No
Data Analysis and Mw Deconvolution
Determination of Mw for each peak in the chromatograms was performed by the provided MaxEnt1 function in the MassLynx software Samples were neutralized as shown below:

0.5M and 1M NaOH: 150 μL of sample+20 μL of 1M dithiothreitol (DTT) & 2M Tris HCl & 10% Formic acid+2.5 μL of formic acid 0.1M NaOH: 200 μL of sample+20 μL 1M DTT & 2M Tris-HCl 0.05M NaOH: 200 μL of sample+10 μL 1M DTT & 2M Tris-HCl 0.5M Acetic acid pH 2.5:150 μL of sample+15 μL 1M DTT & 2M Tris pH 8.5+5 μL of 50% NaOH 0.1M HAc+40% EtOH: 200 μL solution+20 μL 1 M DTT+2M Tris-base (first wash after NaOH has pH 13-14, therefore the sample preparation is done differently: for example, 200 μL sample++10 μL 1M DTT+2 M Tris HCl)

0.5M HAc+40% EtOH: 200 μL solution+20 μL 1 M DTT+2M Tris-base+2.5 μL 50% NaOH 0.025M NaAc pH 5:200 μL of sample+20 μL 1M DTT & 2M Tris-base MQ: 200 μL of sample+20 μL 1M DTT & 2M Tris-HCl Apart from the above samples, the rest of the samples had the same sample preparation as for 0.025M NaAc i.e., 200 μL of sample+20 μL 1M DTT & 2M Tris-base All neutralized samples were incubated for 30 minutes at 37° C. and injected into LC-MS.

The results are presented in Table 1, which shows that 50-1000 mM NaOH is remarkably efficient compared with all other solutions. This is surprising in that the ligand is alkali stable and does not hydrolyse under the conditions used. <LOD (limit of detection) means that no washed-out ligand could be detected.

TABLE 1

Results from screening of wash solutions

| Chemical | Concentration | Ligand concentration (μg/ml) |
|---|---|---|
| Acetic acid (pH 2.5) | 0.5M | <LOD |
| Acetic acid/NaCl (pH 2.5) | 0.5M/150 mM | <LOD |
| Acetic acid/NaCl (pH 2.5) | 0.5M/500 mM | <LOD |
| Acetic acid/EtOH (pH 2.5) | 0.5M/20% | <LOD |
| Acetic acid/EtOH (pH 2.5) | 0.5M/40% | 0.29 |
| Acetate pH 5 | 0.1M | <LOD |
| Acetate/NaCl pH 5 | 0.1M/150 mM | <LOD |
| Acetate/NaCl pH 5 | 0.1M/500 mM | <LOD |
| Acetate/2-propanol pH 5 | 0.1M/30% | <LOD |
| Acetate/2-propanol pH 5 | 0.1M/40% | <LOD |
| Tris/NaCl pH 8.5 | 0.1M/150 mM | <LOD |
| Tris/NaCl pH 8.5 | 0.1M/500 mM | <LOD |
| Tris/NaCl/EtOH pH 8.5 | 0.1M/150 mM/20% | <LOD |
| Tris/NaCl/EtOH pH 8.5 | 0.1M/150 mM/40% | 0.05 |
| Tris/EtOH pH 8.5 | 0.1M/20% | 0.01 |
| Tris/EtOH pH 8.5 | 0.1M/40% | 0.02 |
| Tris/2-propanol pH 8.5 | 0.1M/30% | 0.07 |
| Tris/2-propanol pH 8.5 | 0.1M/40% | 0.12 |
| Ethanol | 20% | 0.004 |
| Ethanol | 40% | 0.05 |
| Ethanol | 70% | <LOD |
| 2-propanol | 30% | <LOD |
| 2-propanol | 40% | <LOD |
| Guanidine hydrochloride | 6M | <LOD |
| Sodium hydroxide | 0.1M | 14 |
| Sodium hydroxide | 0.5M | 13 |
| Sodium hydroxide | 1.0M | 16 |
| MgCl | 1M | <LOD |
| CaCl | 1M | 1 |

TABLE 1-continued

Results from screening of wash solutions

| Chemical | Concentration | Ligand concentration (μg/ml) |
|---|---|---|
| Reducing agent (in Tris pH 8.5) | 100 mM | 0.01 |
| MilliQ ™ water | | 0.04 |
| PBS | | <LOD |

Example 3—Comparison of Removal Efficiency Between NaOH Solutions and HAc/EtOH Solutions The prototype matrix was drained on a glass filter funnel (no 3) and 0.7-0.8 g (mL) filter cake aliquots were packed into empty 10 ml plastic columns (PD-10, GE Healthcare). After incubation for 10 minute cycles (5 cycles, see table 2), eluates were collected and samples analyzed by LC-MS as above. For complete removal of liquid, the resin in each column was drained by applying an air overpressure to the column using a syringe.

TABLE 2

| Wash cycle (10 minutes) | Reference Milli Q water | 100 mM NaOH | 50 mM NaOH | 500 mM Acetic acid + 40% EtOH | 100 mM Acetic acid + 40% EtOH |
|---|---|---|---|---|---|
| Weighed resin amount, g | 0.707 | 0.650 | 0.793 | 0.675 | 0.736 |
| Wash solution volume mL in cycle 1-5 | 0.71 | 0.65 | 0.79 | 0.68 | 0.74 |

Figure 2:
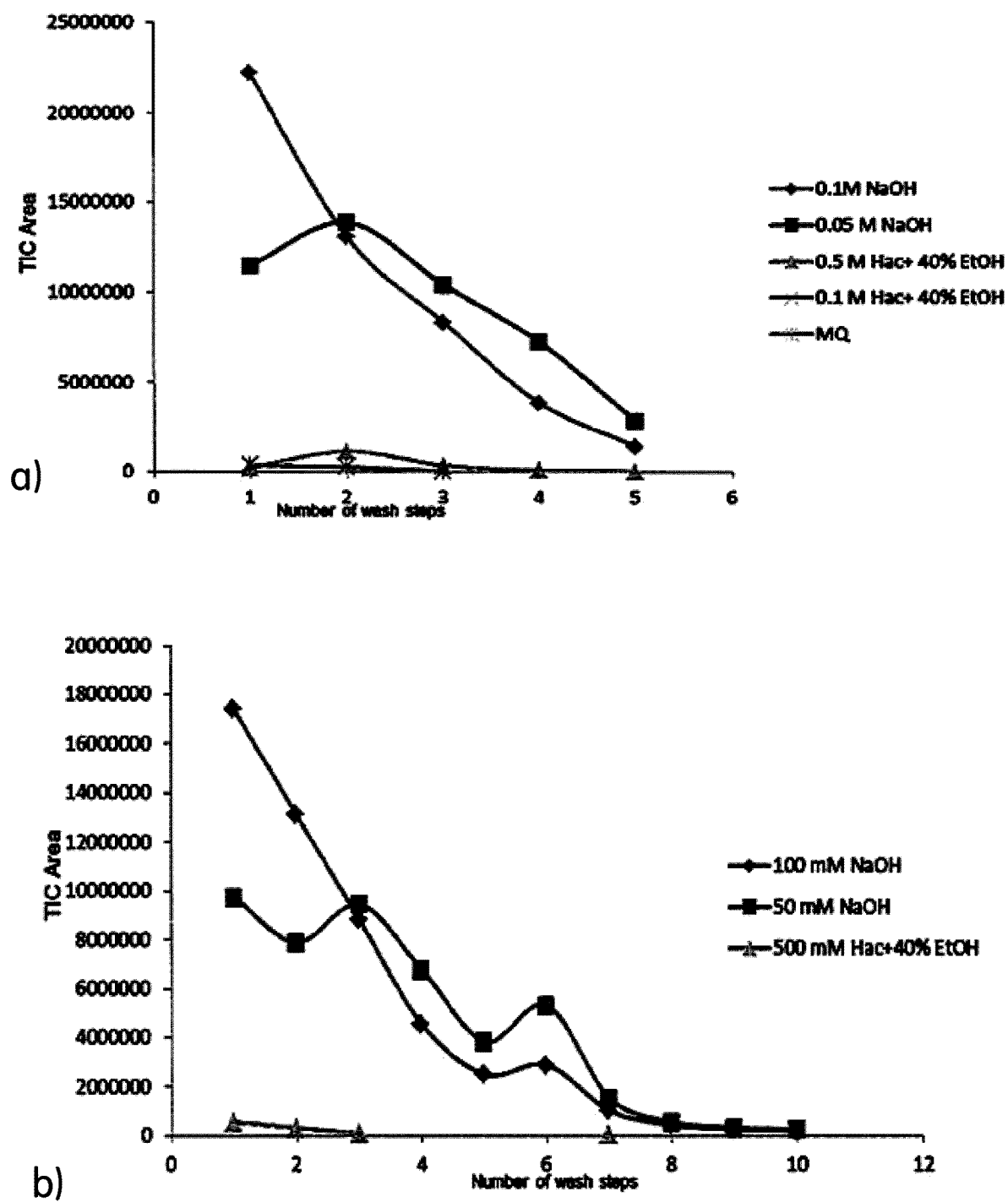
FIG. 2 shows the removal of unbound ligand from an alkali-stable Protein A separation matrix during a) 5 and b) 10 subsequent 10 min wash steps.

The results are shown in FIG. 2 a), which confirms that both 50 and 100 mM NaOH are vastly more efficient than water and the HAc/EtOH solutions.

The experiment was repeated with a 10-cycle setup according to Table 3.

TABLE 3

| Wash cycle (10 minutes) | 50 mM NaOH | 100 mM NaOH | 500 mM Acetic acid + 40% EtOH |
|---|---|---|---|
| Weighed resin amount, g | 0.829 | 0.833 | 0.955 |
| Wash solution volume in mL in cycle 1-10 | 0.83 | 0.83 | 0.96 |

The results from this setup are presented in FIG. 2 b) and show that a plateau level very close to zero has been reached after 10×10 min cycles with either of the NaOH solutions.

Some further experiments were made with 0.1 M NaOH solutions containing 40% ethanol and with prolonging the wash cycles to 30 min instead of 10 min. The results from these experiments were not significantly different from those with 0.1 M NaOH in water with 10 min cycle time.

Example 4—NaOH Wash Followed by HAc/EtOH and NaAc Washes

Example 3 was repeated with a sequence of 10 wash cycles in either 50 or 100 mM NaOH, 3 cycles in 100 mM HAc+40% EtOH and 5 cycles in 25 mM NaAc, pH 5, followed by transfer to a 20% aqueous EtOH storage solution.

| Wash solution/cycle no | Wash solution, mL | Time min |
|---|---|---|
| Weighed resin amount, g | 3.00 | |
| 50/100 mM NaOH #1-10 | 3.00 | 10 |
| 100 mM Acetic acid + 40% EtOH #11-13 | 3.00 | 10 |
| 25 mM NaAc pH 5 #14-18 | 3.00 | 10 |
| 20% EtOH | 3.00 | storage |

Figure 3:
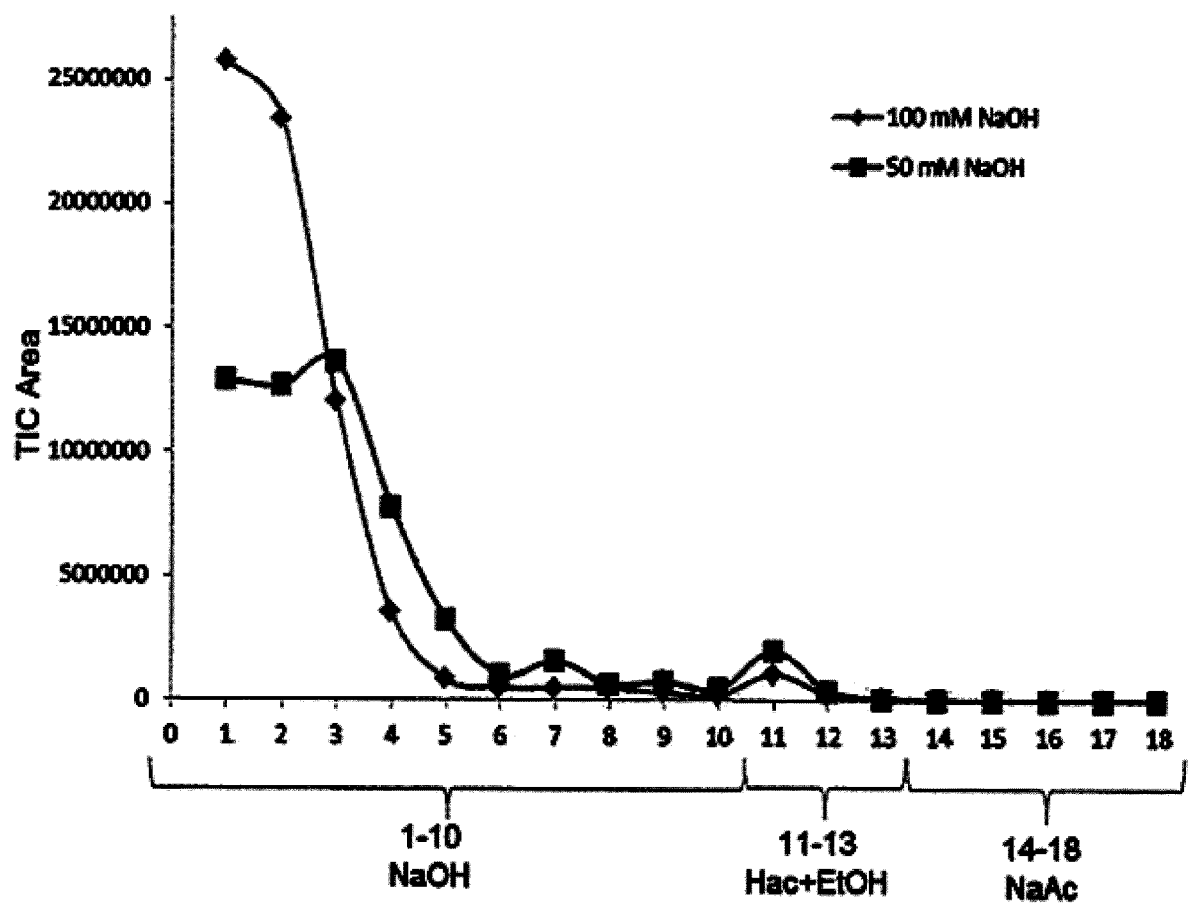
FIG. 3 shows the removal of unbound ligand from an alkali-stable Protein A separation matrix during a sequence of 10 NaOH wash steps, 3 HAc/EtOH steps and 5 NaAc steps.

The results presented in FIG. 3 show that almost all unbound ligand was removed in the NaOH steps, with a small amount occurring in the first HAc/EtOH step.

Example 5—Ligand Leakage—Comparison with Conventional HAc and Buffer Washing Ligand Leakage Test Method 2.0 mL gel sediment was packed in a 5×100 mm Tricorn 5/100 column (GE Healthcare) with 20% ethanol+0.2 M NaCl as the packing liquid and a packing flow of 3.5 mL/min. The bed height was 9.7 cm. The column was equilibrated with 0.020 M $NaH_2PO_4$, pH 7.0 (A-buffer), loaded with 16.65 CV 2 g/L polyclonal human IgG solution (Octapharma Gammanorm) in A-buffer at 6 min residence time, followed by a wash for 3CV with A-buffer and the IgG was eluted with 5 CV of 0.1 M glycine, pH 3.0 (B-buffer) and the eluate collected for later analysis with ELISA. The IgG-containing eluate was pooled and the concentration of leaked ligand in the pool was measured by an ELISA immunoassay for Protein A (Repligen #9000-1).

The sequence of Example 4 resulted in a separation matrix with approximately the same leakage level (<30 ng ligand per mg IgG) as a matrix washed with a reference sequence involving 12×10 min cycles with 0.5 M HAc, 15×10 min cycles with 0.1 M Tris/0.15 M NaCl pH 8.5, 1×17 h cycle with 0.1 M Tris/0.15 M NaCl pH 8.5/20% EtOH, 3×10 min cycles with 0.5 M HAc, 5×10 min cycles with 0.1 M Tris/0.15 M NaCl pH 8.5 and 10×10 min cycles with distilled water before transfer to a 20% aqueous EtOH storage solution. The NaOH method involved 18×10 min cycles with a total time of 3 h, as compared to the reference method with 45×10 min cycles+1×17 h, i.e. with a total time of 24.5 h (7.5 h+17 h).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

SEQUENCE LISTING

```
<160> NUMBER OF SEQ ID NOS: 172

<210> SEQ ID NO 1
<211> LENGTH: 51
<212> TYPE: PRT
<213> ORGANISM: Staphylococcus aureus

<400> SEQUENCE: 1

Ala Gln Gln Asn Ala Phe Tyr Gln Val Leu Asn Met Pro Asn Leu Asn
1               5                   10                  15

Ala Asp Gln Arg Asn Gly Phe Ile Gln Ser Leu Lys Asp Asp Pro Ser
            20                  25                  30

Gln Ser Ala Asn Val Leu Gly Glu Ala Gln Lys Leu Asn Asp Ser Gln
        35                  40                  45

Ala Pro Lys
    50

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

```
Lys Lys Leu Asn Asp Ala Gln Ala Pro Lys
    50                  55
```

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 7

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 8

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Ala Leu Leu Ala Glu Ala
        35                  40                  45

Lys Lys Leu Asn Asp Ala Gln Ala Pro Lys
    50                  55
```

<210> SEQ ID NO 9
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 9

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Ala Ala Phe Ile Gln
            20                  25                  30

Ser Leu Lys Asp Asp Pro Ser Gln Ser Ala Ala Leu Leu Ala Glu Ala
        35                  40                  45

Lys Lys Leu Asn Asp Ala Gln Ala Pro Lys
    50                  55
```

<210> SEQ ID NO 10
<211> LENGTH: 58
<212> TYPE: PRT
<213> ORGANISM: Artificial Sequence
<220> FEATURE:

```
<223> OTHER INFORMATION: Description of Artificial Sequence: Synthetic
      Mutated Protein A domain sequence

<400> SEQUENCE: 10

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 11

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 12

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Ala
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 13

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Gln
            20                  25                  30
```

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 14

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Glu
            20                  25                  30

Ser Leu Lys Asp Asp Pro Ser Glu Ser Ala Asn Leu Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 15

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Glu
            20                  25                  30

Ser Leu Lys Asp Asp Pro Ser Gln Ser Ala Asn Leu Leu Ala Glu Ala
        35                  40                  45

Lys Arg Leu Asn Asp Ala Gln Ala Pro Lys
    50                  55

<210> SEQ ID NO 16
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 16

Val Asp Ala Lys Phe Asp Lys Glu Gln Gln Lys Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58

```
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 17

Val Asp Ala Lys Phe Asp Lys Glu Gln Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 18

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Ala Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 19

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Ala Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 20

Val Asp Ala Lys Phe Asp Lys Glu Gln Gln Lys Ala Phe Tyr Glu Ile
1               5                   10                  15
```

-continued

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 21

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 22

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Arg Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 23

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Asn Leu Leu Ala Glu Ala
        35                  40                  45

Lys Lys Leu Asn Asp Ala Gln Ala Pro Lys
    50                  55

```
<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 24

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 25

Ala Asp Asn Lys Phe Asn Lys Glu Ala Gln Glu Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 26

Val Asp Ala Lys Phe Asp Lys Glu Gln Gln Tyr Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 27
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 27
```

Val Asp Ala Lys Phe Asp Lys Glu Gln Gln Thr Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 28
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 28

Val Asp Ala Lys Phe Asp Lys Glu Gln Gln Phe Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 29
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 29

Val Asp Ala Lys Phe Asp Lys Glu Gln Gln Leu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 30
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 30

Val Asp Ala Lys Phe Asp Lys Glu Gln Gln Trp Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 31
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 31

Val Asp Ala Lys Phe Asp Lys Glu Gln Gln Ile Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 32

Val Asp Ala Lys Phe Asp Lys Glu Gln Gln Met Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 33

Val Asp Ala Lys Phe Asp Lys Glu Gln Gln Val Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 34
<211> LENGTH: 58
<212> TYPE: PRT
<213> ORGANISM: Artificial Sequence
<220> FEATURE:
<223> OTHER INFORMATION: Description of Artificial Sequence: Synthetic Mutated Protein A domain sequence

<400> SEQUENCE: 34

Val Asp Ala Lys Phe Asp Lys Glu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 35
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 35

Val Asp Ala Lys Phe Asp Lys Glu Gln Gln His Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 36
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 36

Val Asp Ala Lys Phe Asp Lys Glu Gln Gln Arg Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 37

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Val Ser Lys Ala Ile Leu Ala Glu Ala
            35                  40                  45

Lys Lys Leu Asn Asp Ala Gln Ala Pro Lys
        50                  55

<210> SEQ ID NO 38
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 38

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Val Ser Arg Ala Ile Leu Ala Glu Ala
            35                  40                  45

Lys Lys Leu Asn Asp Ala Gln Ala Pro Lys
        50                  55

<210> SEQ ID NO 39
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 39

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Ala Ile Leu Ala Glu Ala
            35                  40                  45

Lys Lys Leu Asn Asp Ala Gln Ala Pro Lys
        50                  55

<210> SEQ ID NO 40
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 40

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ser Phe Ile Gln
            20                  25                  30

Ser Leu Lys Asp Asp Pro Ser Val Ser Lys Ala Ile Leu Ala Glu Ala
            35                  40                  45

Lys Lys Leu Asn Asp Ala Gln Ala Pro Lys
        50                  55

<210> SEQ ID NO 41
<211> LENGTH: 58
<212> TYPE: PRT

<213> ORGANISM: Artificial Sequence
<220> FEATURE:
<223> OTHER INFORMATION: Description of Artificial Sequence: Synthetic
      Mutated Protein A domain sequence

<400> SEQUENCE: 41

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Tyr Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 42
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 42

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Gln Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 43
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 43

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Thr Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 44
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 44

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Asn Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 45
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 45

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Phe Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 46

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Leu Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 47
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 47

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Trp Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

```
<210> SEQ ID NO 48
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 48

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ile Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 49
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 49

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Met Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 50
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 50

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Val Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 51
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 51
```

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Asp Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55
```

<210> SEQ ID NO 52
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 52

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Glu Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55
```

<210> SEQ ID NO 53
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 53

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn His Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55
```

<210> SEQ ID NO 54
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 54

```
Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Arg Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
```

```
          50                  55

<210> SEQ ID NO 55
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 55

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 56
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 56

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Phe Ala Gln Ala Pro Lys
    50                  55

<210> SEQ ID NO 57
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 57

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Tyr Ala Gln Ala Pro Lys
    50                  55

<210> SEQ ID NO 58
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence
```

<400> SEQUENCE: 58

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Trp Ala Gln Ala Pro Lys
    50                  55

<210> SEQ ID NO 59
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 59

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Lys Ala Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 60

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Arg Ala Gln Ala Pro Lys
    50                  55

<210> SEQ ID NO 61
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 61

Val Asp Ala Lys Phe Asp Lys Glu Gln Glu Ala Phe Tyr Glu Ile Leu
1               5                   10                  15

His Leu Pro Asn Leu Thr Glu Glu Gln Arg Asn Ala Phe Ile Gln Ser
            20                  25                  30

Leu Lys Asp Asp Pro Ser Val Ser Lys Ala Ile Leu Ala Glu Ala Lys

```
                35                  40                  45

Lys Leu Asn Asp Ala Gln Ala Pro Lys
    50                  55

<210> SEQ ID NO 62
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 62

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Ser Lys Ala Ile Leu Ala Glu Ala Lys
        35                  40                  45

Lys Leu Asn Asp Ala Gln Ala Pro Lys
    50                  55

<210> SEQ ID NO 63
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 63

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Ala Ile Leu Ala Glu Ala Lys
        35                  40                  45

Lys Leu Asn Asp Ala Gln Ala Pro Lys
    50                  55

<210> SEQ ID NO 64
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 64

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ile Leu Ala Glu Ala Lys
        35                  40                  45

Lys Leu Asn Asp Ala Gln Ala Pro Lys
    50                  55

<210> SEQ ID NO 65
<211> LENGTH: 55
<212> TYPE: PRT
<213> ORGANISM: Artificial Sequence
```

```
<220> FEATURE:
<223> OTHER INFORMATION: Description of Artificial Sequence: Synthetic
      Mutated Protein A domain sequence

<400> SEQUENCE: 65

Val Phe Asp Lys Glu Ala Gln Glu Ala Phe Tyr Glu Ile Leu His Leu
1               5                   10                  15

Pro Asn Leu Thr Glu Glu Gln Arg Asn Ala Phe Ile Gln Ser Leu Lys
            20                  25                  30

Asp Asp Pro Ser Val Ser Lys Ala Ile Leu Ala Glu Ala Lys Lys Leu
        35                  40                  45

Asn Asp Ala Gln Ala Pro Lys
    50                  55

<210> SEQ ID NO 66
<211> LENGTH: 55
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 66

Ala Lys Phe Asp Lys Glu Ala Gln Glu Ala Phe Tyr Glu Ile Leu His
1               5                   10                  15

Leu Pro Asn Leu Thr Glu Glu Gln Arg Asn Ala Phe Ile Gln Ser Leu
            20                  25                  30

Lys Asp Asp Pro Ser Val Ser Lys Ala Ile Leu Ala Glu Ala Lys Lys
        35                  40                  45

Leu Asn Asp Ala Gln Ala Pro
    50                  55

<210> SEQ ID NO 67
<211> LENGTH: 53
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 67

Val Asp Ala Ala Gln Glu Ala Phe Tyr Glu Ile Leu His Leu Pro Asn
1               5                   10                  15

Leu Thr Glu Glu Gln Arg Asn Ala Phe Ile Gln Ser Leu Lys Asp Asp
            20                  25                  30

Pro Ser Val Ser Lys Ala Ile Leu Ala Glu Ala Lys Lys Leu Asn Asp
        35                  40                  45

Ala Gln Ala Pro Lys
    50

<210> SEQ ID NO 68
<211> LENGTH: 55
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 68

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
```

```
                 20                  25                  30

Ser Leu Lys Asp Asp Pro Ser Val Ser Lys Ala Ile Leu Ala Glu Ala
             35                  40                  45

Lys Lys Leu Asn Asp Ala Gln
         50                  55

<210> SEQ ID NO 69
<211> LENGTH: 55
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 69

Lys Phe Asp Lys Glu Ala Gln Glu Ala Phe Tyr Glu Ile Leu His Leu
1               5                  10                  15

Pro Asn Leu Thr Glu Glu Gln Arg Asn Ala Phe Ile Gln Ser Leu Lys
                 20                  25                  30

Asp Asp Pro Ser Val Ser Lys Ala Ile Leu Ala Glu Ala Lys Lys Leu
             35                  40                  45

Asn Asp Ala Gln Ala Pro Lys
         50                  55

<210> SEQ ID NO 70
<211> LENGTH: 50
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 70

Ala Gln Glu Ala Phe Tyr Glu Ile Leu His Leu Pro Asn Leu Thr Glu
1               5                  10                  15

Glu Gln Arg Asn Ala Phe Ile Gln Ser Leu Lys Asp Asp Pro Ser Val
                 20                  25                  30

Ser Lys Ala Ile Leu Ala Glu Ala Lys Lys Leu Asn Asp Ala Gln Ala
             35                  40                  45

Pro Lys
     50

<210> SEQ ID NO 71
<211> LENGTH: 62
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 71

Val Asp Ala Lys Phe Asp Lys Glu Ala Gln Glu Ala Phe Tyr Glu Ile
1               5                  10                  15

Leu His Leu Pro Asn Leu Thr Glu Glu Gln Arg Asn Ala Phe Ile Gln
                 20                  25                  30

Ser Leu Lys Asp Asp Pro Ser Val Ser Lys Ala Ile Leu Ala Glu Ala
             35                  40                  45

Lys Lys Leu Asn Asp Ala Gln Ala Pro Lys Tyr Glu Asp Gly
         50                  55                  60

<210> SEQ ID NO 72
```

```
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 72

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 73
<211> LENGTH: 54
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 73

Ala Asp Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 74
<211> LENGTH: 54
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 74

Ala Asp Lys Glu Gln Gln Asn Ala Phe Tyr Glu Ile Leu His Leu Pro
1               5                   10                  15

Asn Leu Thr Glu Glu Gln Arg Asn Ala Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 75
<211> LENGTH: 54
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 75

Phe Asn Lys Glu Gln Gln Asn Ala Phe Tyr Glu Ile Leu His Leu Pro
```

-continued

```
                1               5                  10                  15
Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50
```

<210> SEQ ID NO 76
<211> LENGTH: 55
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 76

```
Lys Phe Asn Lys Glu Gln Gln Asn Ala Phe Tyr Glu Ile Leu His Leu
1               5                  10                  15

Pro Asn Leu Thr Glu Glu Gln Arg Asn Gly Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys
    50                  55
```

<210> SEQ ID NO 77
<211> LENGTH: 54
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 77

```
Phe Asn Lys Glu Gln Gln Asn Ala Phe Tyr Glu Ile Leu His Leu Pro
1               5                  10                  15

Asn Leu Thr Glu Glu Gln Arg Asn Lys Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50
```

<210> SEQ ID NO 78
<211> LENGTH: 55
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 78

```
Lys Phe Asn Lys Glu Gln Gln Asn Ala Phe Tyr Glu Ile Leu His Leu
1               5                  10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys
    50                  55
```

<210> SEQ ID NO 79
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 79

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 80
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 80

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Glu Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 81
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 81

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Arg Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 82
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

```
<400> SEQUENCE: 82

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ile Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 83
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 83

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Leu Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 84
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 84

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Phe Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 85
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 85

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Tyr Phe Ile Gln
            20                  25                  30

Ser Leu Lys Asp Asp Pro Ser Val Ser Lys Glu Ile Leu Ala Glu Ala
        35                  40                  45
```

-continued

Lys Lys Leu Asn Asp Ala Gln Ala Pro Lys
    50                  55

<210> SEQ ID NO 86
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 86

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Met Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 87
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 87

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Trp Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 88
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 88

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Val Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 89
<211> LENGTH: 58
<212> TYPE: PRT
<213> ORGANISM: Artificial Sequence
<220> FEATURE:

<223> OTHER INFORMATION: Description of Artificial Sequence: Synthetic
      Mutated Protein A domain sequence

<400> SEQUENCE: 89

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Thr Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 90
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 90

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Asp Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 91
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 91

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn His Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 92
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 92

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ser Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 93
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 93

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 94
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 94

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Thr Asn Val Leu Gly Glu Ala
        35                  40                  45

Lys Lys Leu Asn Asp Ala Gln Ala Pro Lys
    50                  55

<210> SEQ ID NO 95
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 95

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Lys
            20                  25                  30

Ser Ile Arg Asp Asp Pro Ser Gln Ser Thr Asn Val Leu Gly Glu Ala
        35                  40                  45

Lys Lys Leu Asn Asp Ala Gln Ala Pro Lys
    50                  55

<210> SEQ ID NO 96
<211> LENGTH: 59

```
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 96

Val Asp Asn Phe Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 97
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 97

Val Asp Asn Leu Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 98

Val Asp Asn Ile Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 99
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 99

Val Asp Asn Pro Lys Phe Asn Lys Glu Gln Gln Asn Ala Phe Tyr Glu
1               5                   10                  15
```

```
Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 100
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 100

Val Asp Asn Gln Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 101
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 101

Val Asp Asn His Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 102
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 102

Val Asp Asn Arg Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55
```

<210> SEQ ID NO 103
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 103

Val Asp Asn Thr Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 104
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 104

Val Asp Asn Tyr Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 105
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 105

Val Asp Asn Ala Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 106
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 106

Val Asp Asn Met Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 107
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 107

Val Asp Asn Asp Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 108
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 108

Val Asp Asn Trp Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 109
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 109

Val Asp Asn Glu Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 110
<211> LENGTH: 59
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 110

Val Asp Asn Val Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys
    50                  55

<210> SEQ ID NO 111
<211> LENGTH: 60
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 111

Val Asp Asn Ile Thr Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys
    50                  55                  60

<210> SEQ ID NO 112
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 112

Val Asp Asn Lys Phe Asn Lys Glu Gln Gln Asn Ala Phe Tyr Glu Ile
1               5                   10                  15

Leu His Leu Pro Asn Leu His Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 113
<211> LENGTH: 58
<212> TYPE: PRT
<213> ORGANISM: Artificial Sequence
<220> FEATURE:
<223> OTHER INFORMATION: Description of Artificial Sequence: Synthetic Mutated Protein A domain sequence

<400> SEQUENCE: 113

Val Asp Asn Lys Phe Asn Lys Glu Gln Gln Asn Ala Phe Tyr Glu Ile
1               5                   10                  15

Leu His Leu Pro Asn Leu Ser Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 114
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 114

Val Asp His Lys Phe Asn Lys Glu Gln Gln Asn Ala Phe Tyr Glu Ile
1               5                   10                  15

Leu His Leu Pro Asn Leu Ser Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 115
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 115

Val Asp His Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 116
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 116

Val Asp His Lys Phe Asp Lys Glu Gln Gln Asn Ala Phe Tyr Glu Ile
1               5                   10                  15

Leu His Leu Pro Asn Leu Ser Glu Glu Gln Arg Asn Ala Phe Ile Gln
            20                  25                  30

```
Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 117
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 117

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Lys
    50                  55

<210> SEQ ID NO 118
<211> LENGTH: 57
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 118

Val Asp Asp Lys Phe Leu Lys Glu Gln Gln Asn Ala Phe Tyr Glu Ile
1               5                   10                  15

Leu His Pro Asn Leu Thr Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys
    50                  55

<210> SEQ ID NO 119
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 119

Val Asp Ala Lys Phe Asp Lys Glu Ala Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 120
<211> LENGTH: 58
<212> TYPE: PRT
```

```
<213> ORGANISM: Artificial Sequence
<220> FEATURE:
<223> OTHER INFORMATION: Description of Artificial Sequence: Synthetic
      Mutated Protein A domain sequence

<400> SEQUENCE: 120

Val Asp Ala Lys Phe Asp Lys Glu Ala Gln Asn Ala Phe Tyr Lys Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 121
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 121

Val Asp Ala Lys Phe Asp Lys Glu Ala Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Thr Ala
        35                  40                  45

Lys Lys Leu Asn Asp Ala Gln Ala Pro Lys
    50                  55

<210> SEQ ID NO 122
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 122

Val Asp Ala Lys Phe Asp Lys Glu Ala Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Thr Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 123
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 123

Val Asp Ala Lys Phe Asp Lys Glu Ala Gln Asn Ala Phe Tyr Glu Ile
1               5                   10                  15
```

Leu His Leu Pro Asn Leu Thr Glu Glu Gln Arg Asn Ala Phe Ile Gln
            20                  25                  30

Ser Leu Lys Ala Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 124
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 124

Val Asp Ala Lys Phe Asp Lys Glu Thr Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Thr Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 125
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 125

Val Asp Ala Lys Phe Asp Lys Glu Ala Gln Asn Ala Phe Tyr Glu Ile
1               5                   10                  15

Leu His Leu Pro Asn Leu Thr Glu Glu Ala Arg Asn Ala Phe Ile Gln
            20                  25                  30

Ser Leu Lys Ala Asp Pro Ser Gln Ser Ala Asn Leu Leu Ala Ala Ala
        35                  40                  45

Lys Lys Leu Asn Asp Ala Gln Ala Pro Lys
    50                  55

<210> SEQ ID NO 126
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 126

Val Asp Ala Lys Phe Asp Lys Glu Ala Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Thr Ala
        35                  40                  45

Glu Lys Leu Ser Asp Ala Gln Ala Pro Lys
    50                  55

```
<210> SEQ ID NO 127
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 127

Val Asp Ala Lys Phe Asp Lys Glu Thr Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Thr Ala
        35                  40                  45

Lys Lys Leu Asn Asp Ala Gln Ala Pro Lys
    50                  55

<210> SEQ ID NO 128
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 128

Val Asp Ala Lys Phe Asp Lys Glu Trp Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 129
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 129

Val Asp Ala Lys Phe Asp Lys Glu Leu Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 130
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 130
```

Val Asp Ala Lys Phe Asp Lys Glu Glu Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 131
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 131

Val Asp Ala Lys Phe Asp Lys Glu Lys Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 132
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 132

Val Asp Ala Lys Phe Asp Lys Glu Val Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 133
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 133

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Arg Asn Leu Leu Ala Glu Ala
        35                  40                  45

Lys Lys Leu Asn Asp Ala Gln Ala Pro Lys 50              55

<210> SEQ ID NO 134
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 134

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 135
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 135

Val Asp Ala Lys Phe Asp Lys Glu Gln Gln Asn Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 136
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 136

Val Asp Ala Lys Phe Asp Lys Glu Gln Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 137
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

```
<400> SEQUENCE: 137

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 138
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 138

Val Asp Ala Lys Phe Asp Lys Glu Gln Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 139
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 139

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 140
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 140

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Ala Ile Gln
            20                  25                  30

Ser Leu Lys Asp Asp Pro Ser Gln Ser Ala Asn Leu Leu Ala Glu Ala
```

```
                35                  40                  45

Lys Lys Leu Asn Asp Ala Gln Ala Pro Lys
    50                  55

<210> SEQ ID NO 141
<211> LENGTH: 58
<212> TYPE: PRT
<213> ORGANISM: Artificial Sequence
<220> FEATURE:
<223> OTHER INFORMATION: Description of Artificial Sequence: Synthetic
      Mutated Protein A domain sequence

<400> SEQUENCE: 141

Val Asp Asn Gly Phe Asn Lys Glu Gln Gln Asn Ala Phe Tyr Glu Ile
1               5                   10                  15

Leu His Leu Pro Asn Leu Thr Glu Glu Gln Arg Asn Ala Ala Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: Synthetic
      Leader sequence

<400> SEQUENCE: 142

Ala Gln Gly Thr
1

<210> SEQ ID NO 143
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant protein A domain sequence

<400> SEQUENCE: 143

Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys
    50                  55

<210> SEQ ID NO 144
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant protein A domain sequence

<400> SEQUENCE: 144

Ile Ala Ala Gln His Asp Lys Asp Gln Gln Ala Ala Phe Tyr Glu Ile
1               5                   10                  15
```

```
Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55
```

<210> SEQ ID NO 145
<211> LENGTH: 58
<212> TYPE: PRT
<213> ORGANISM: Artificial Sequence
<220> FEATURE:
<223> OTHER INFORMATION: Description of Artificial Sequence: Synthetic
    mutant protein A domain sequence

<400> SEQUENCE: 145

```
Ile Ala Ala Gln His Asp Lys Glu His Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys
    50                  55
```

<210> SEQ ID NO 146
<211> LENGTH: 58
<212> TYPE: PRT
<213> ORGANISM: Artificial Sequence
<220> FEATURE:
<223> OTHER INFORMATION: Description of Artificial Sequence: Synthetic
    mutant protein A domain sequence

<400> SEQUENCE: 146

```
Ile Ala Ala Gln His Asp Lys Asp His Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55
```

<210> SEQ ID NO 147
<211> LENGTH: 58
<212> TYPE: PRT
<213> ORGANISM: Artificial Sequence
<220> FEATURE:
<223> OTHER INFORMATION: Description of Artificial Sequence: Synthetic
    mutant protein A domain sequence

<400> SEQUENCE: 147

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg His Asp Pro Ser Val Ser Leu Glu Ile Leu Gly Glu Ala
        35                  40                  45

Lys Lys Leu Asn Asp Ala Gln Ala Pro Lys
    50                  55
```

```
<210> SEQ ID NO 148
<211> LENGTH: 58
<212> TYPE: PRT
<213> ORGANISM: Artificial Sequence
<220> FEATURE:
<223> OTHER INFORMATION: Description of Artificial Sequence: Synthetic
      mutant protein A domain sequence

<400> SEQUENCE: 148

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg His Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 149
<211> LENGTH: 72
<212> TYPE: PRT
<213> ORGANISM: Peptostreptococcus magnus

<400> SEQUENCE: 149

Ser Glu Glu Glu Val Thr Ile Lys Ala Asn Leu Ile Phe Ala Asn Gly
1               5                   10                  15

Ser Thr Gln Thr Ala Glu Phe Lys Gly Thr Phe Glu Lys Ala Thr Ser
            20                  25                  30

Glu Ala Tyr Ala Tyr Ala Asp Thr Leu Lys Lys Asp Asn Gly Glu Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70

<210> SEQ ID NO 150
<211> LENGTH: 72
<212> TYPE: PRT
<213> ORGANISM: Peptostreptococcus magnus

<400> SEQUENCE: 150

Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Ala Leu Lys Lys Asp Asn Gly Glu Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70

<210> SEQ ID NO 151
<211> LENGTH: 72
<212> TYPE: PRT
<213> ORGANISM: Peptostreptococcus magnus

<400> SEQUENCE: 151

Pro Lys Glu Glu Val Thr Ile Lys Ala Asn Leu Ile Tyr Ala Asp Gly
1               5                   10                  15
```

Lys Thr Gln Thr Ala Glu Phe Lys Gly Thr Phe Glu Ala Thr Ala
            20                  25                  30

Glu Ala Tyr Arg Tyr Ala Asp Leu Leu Ala Lys Glu Asn Gly Lys Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70

<210> SEQ ID NO 152
<211> LENGTH: 73
<212> TYPE: PRT
<213> ORGANISM: Peptostreptococcus magnus

<400> SEQUENCE: 152

Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Ala Glu Ala Thr Ala
            20                  25                  30

Glu Ala Tyr Arg Tyr Ala Asp Leu Leu Ala Lys Glu Asn Gly Lys Tyr
        35                  40                  45

Thr Ala Asp Leu Glu Asp Gly Gly Tyr Thr Ile Asn Ile Arg Phe Ala
    50                  55                  60

Gly Lys Lys Val Asp Glu Lys Pro Glu
65                  70

<210> SEQ ID NO 153
<211> LENGTH: 65
<212> TYPE: PRT
<213> ORGANISM: Peptostreptococcus magnus

<400> SEQUENCE: 153

Glu Lys Glu Gln Val Thr Ile Lys Glu Asn Ile Tyr Phe Glu Asp Gly
1               5                   10                  15

Thr Val Gln Thr Ala Thr Phe Lys Gly Thr Phe Ala Glu Ala Thr Ala
            20                  25                  30

Glu Ala Tyr Arg Tyr Ala Asp Leu Leu Ser Lys Glu His Gly Lys Tyr
        35                  40                  45

Thr Ala Asp Leu Glu Asp Gly Gly Tyr Thr Ile Asn Ile Arg Phe Ala
    50                  55                  60

Gly
65

<210> SEQ ID NO 154
<211> LENGTH: 72
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 154

Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
        35                  40                  45

Thr Val Asp Val Ala Asp Lys Gly Tyr Thr Leu Asn Ile Lys Phe Ala

```
                  50                  55                  60

Gly Lys Glu Lys Thr Pro Glu Glu
 65                  70

<210> SEQ ID NO 155
<211> LENGTH: 72
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 155

Pro Lys Glu Glu Val Thr Ile Lys Ala Asn Leu Ile Tyr Ala Asp Gly
  1               5                  10                  15

Lys Thr Gln Thr Ala Glu Phe Lys Gly Thr Phe Glu Glu Ala Thr Ala
                 20                  25                  30

Glu Ala Tyr Arg Tyr Ala Asp Leu Leu Ala Lys Glu Ala Gly Lys Tyr
             35                  40                  45

Thr Val Asp Val Ala Asp Lys Gly Tyr Thr Leu Gln Ile Lys Phe Ala
         50                  55                  60

Gly Lys Glu Lys Thr Pro Glu Glu
 65                  70

<210> SEQ ID NO 156
<211> LENGTH: 72
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 156

Pro Lys Glu Glu Val Thr Ile Lys Ala Gln Leu Ile Tyr Ala Asp Gly
  1               5                  10                  15

Lys Thr Gln Thr Ala Glu Phe Lys Gly Thr Phe Glu Glu Ala Thr Ala
                 20                  25                  30

Glu Ala Tyr Arg Tyr Ala Asp Leu Leu Ala Lys Glu Ala Gly Lys Tyr
             35                  40                  45

Thr Val Asp Val Ala Asp Lys Gly Tyr Thr Leu Gln Ile Lys Phe Ala
         50                  55                  60

Gly Lys Glu Lys Thr Pro Glu Glu
 65                  70

<210> SEQ ID NO 157
<211> LENGTH: 70
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 157

Glu Thr Pro Glu Glu Pro Arg Glu Glu Val Thr Ile Arg Val Asn Leu
  1               5                  10                  15

Ile Phe Ala Asp Gly Arg Ile Gln Thr Ala Glu Phe Arg Gly Thr Phe
                 20                  25                  30

Glu Glu Ala Thr Ala Lys Ala Tyr Ala Tyr Ala Asn Leu Leu Ala Lys
             35                  40                  45

Glu Asn Gly Glu Tyr Thr Ala Asp Leu Glu Asp Gly Gly Asn Thr Ile
         50                  55                  60
```

```
Asn Ile Lys Phe Ala Gly
 65                  70

<210> SEQ ID NO 158
<211> LENGTH: 60
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 158

Val Thr Ile Lys Ala Asn Leu Ile Phe Ala Asn Gly Ser Thr Gln Thr
 1               5                  10                  15

Ala Glu Phe Lys Gly Thr Phe Glu Lys Ala Thr Ser Glu Ala Tyr Ala
            20                  25                  30

Tyr Ala Asp Thr Leu Lys Lys Asp Asn Gly Glu Tyr Thr Val Asp Val
        35                  40                  45

Ala Asp Lys Gly Tyr Thr Leu Asn Ile Lys Phe Ala
    50                  55                  60

<210> SEQ ID NO 159
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein L domain sequence

<400> SEQUENCE: 159

Thr Thr Tyr Lys Leu Ile Leu Asp Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 160
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 160

Thr Thr Tyr Lys Leu Ile Leu Leu Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 161
<211> LENGTH: 56
<212> TYPE: PRT
<213> ORGANISM: Artificial Sequence
<220> FEATURE:
```

<223> OTHER INFORMATION: Description of Artificial Sequence: Synthetic
      mutant protein G domain sequence

<400> SEQUENCE: 161

Thr Thr Tyr Lys Leu Ile Leu Ile Gly Lys Thr Leu Thr Gly Tyr Thr
1               5                   10                  15

Thr Thr Ile Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 162
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 162

Thr Thr Tyr Lys Leu Ile Leu Lys Gly Lys Thr Leu Thr Gly Tyr Thr
1               5                   10                  15

Thr Thr Ile Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 163
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 163

Thr Thr Tyr Lys Leu Ile Leu Ile Gly Lys Thr Leu Thr Gly Tyr Thr
1               5                   10                  15

Thr Thr Ile Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 164
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 164

Thr Thr Tyr Lys Leu Ile Val Lys Gly Asn Thr Phe Ser Gly Glu Thr
1               5                   10                  15

Thr Thr Lys Ala Val Asp Ala Glu Thr Ala Glu Lys Ala Phe Lys Gln
            20                  25                  30

```
Tyr Ala Thr Ala Asn Asn Val Asp Gly Glu Trp Ser Tyr Asp Asp Ala
        35                  40                  45

Thr Lys Thr Phe Thr Val Thr Glu
    50                  55

<210> SEQ ID NO 165
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 165

Thr Thr Tyr Lys Leu Ile Val Lys Gly Asn Thr Phe Ser Gly Glu Thr
1               5                   10                  15

Thr Thr Lys Ala Ile Asp Ala Ala Thr Ala Glu Lys Glu Phe Lys Gln
            20                  25                  30

Tyr Ala Thr Ala Asn Gly Val Asp Gly Glu Trp Ser Tyr Asp Asp Ala
        35                  40                  45

Thr Lys Thr Phe Thr Val Thr Glu
    50                  55

<210> SEQ ID NO 166
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 166

Thr Thr Tyr Lys Leu Ile Val Lys Gly Asn Thr Leu Thr Gly Tyr Thr
1               5                   10                  15

Thr Thr Ile Ala Val Asp Ala Glu Thr Ala Glu Lys Ala Leu Lys Gln
            20                  25                  30

Phe Ala Asn Glu Asn Gly Val Tyr Gly Glu Trp Ser Tyr Asp Asp Ala
        35                  40                  45

Thr Lys Thr Phe Thr Val Thr Glu
    50                  55

<210> SEQ ID NO 167
<211> LENGTH: 56
<212> TYPE: PRT
<213> ORGANISM: Artificial Sequence
<220> FEATURE:
<223> OTHER INFORMATION: Description of Artificial Sequence: Synthetic
      mutant protein G domain sequence

<400> SEQUENCE: 167

Thr Thr Tyr Arg Leu Val Ile Lys Gly Val Thr Leu Thr Gly Tyr Thr
1               5                   10                  15

Ala Thr Ile Ala Val Asp Ala Ala Thr Ala Glu Gln Thr Leu Arg Gln
            20                  25                  30

Phe Ala Asn Asp Asn Gly Ile Thr Gly Glu Trp Ala Tyr Asp Thr Ala
        35                  40                  45

Thr Lys Thr Phe Thr Val Thr Glu
    50                  55

<210> SEQ ID NO 168
<211> LENGTH: 72
```

<212> TYPE: PRT
<213> ORGANISM: Peptostreptococcus magnus

<400> SEQUENCE: 168

Pro Glu Glu Glu Val Thr Ile Lys Ala Asn Leu Ile Phe Ala Asp Gly
1               5                   10                  15

Ser Thr Gln Asn Ala Glu Phe Lys Gly Thr Phe Ala Lys Ala Val Ser
            20                  25                  30

Asp Ala Tyr Ala Tyr Ala Asp Ala Leu Lys Lys Asp Asn Gly Glu Tyr
        35                  40                  45

Thr Val Asp Val Ala Asp Lys Gly Leu Thr Leu Asn Ile Lys Phe Ala
    50                  55                  60

Gly Lys Lys Glu Lys Pro Glu Glu
65                  70

<210> SEQ ID NO 169
<211> LENGTH: 74
<212> TYPE: PRT
<213> ORGANISM: Peptostreptococcus magnus

<400> SEQUENCE: 169

Pro Lys Glu Glu Val Thr Ile Lys Val Asn Leu Ile Phe Ala Asp Gly
1               5                   10                  15

Lys Thr Gln Thr Ala Glu Phe Lys Gly Thr Phe Glu Glu Ala Thr Ala
            20                  25                  30

Lys Ala Tyr Ala Tyr Ala Asp Leu Leu Ala Lys Glu Asn Gly Glu Tyr
        35                  40                  45

Thr Ala Asp Leu Glu Asp Gly Gly Asn Thr Ile Asn Ile Lys Phe Ala
    50                  55                  60

Gly Lys Glu Thr Pro Glu Thr Pro Glu Glu
65                  70

<210> SEQ ID NO 170
<211> LENGTH: 74
<212> TYPE: PRT
<213> ORGANISM: Peptostreptococcus magnus

<400> SEQUENCE: 170

Pro Lys Glu Glu Val Thr Ile Lys Val Asn Leu Ile Phe Ala Asp Gly
1               5                   10                  15

Lys Ile Gln Thr Ala Glu Phe Lys Gly Thr Phe Glu Glu Ala Thr Ala
            20                  25                  30

Lys Ala Tyr Ala Tyr Ala Asn Leu Leu Ala Lys Glu Asn Gly Glu Tyr
        35                  40                  45

Thr Ala Asp Leu Glu Asp Gly Gly Asn Thr Ile Asn Ile Lys Phe Ala
    50                  55                  60

Gly Lys Glu Thr Pro Glu Thr Pro Glu Glu
65                  70

<210> SEQ ID NO 171
<211> LENGTH: 74
<212> TYPE: PRT
<213> ORGANISM: Peptostreptococcus magnus

<400> SEQUENCE: 171

Pro Lys Glu Glu Val Thr Ile Lys Val Asn Leu Ile Phe Ala Asp Gly
1               5                   10                  15

Lys Thr Gln Thr Ala Glu Phe Lys Gly Thr Phe Glu Glu Ala Thr Ala
            20                  25                  30

```
Glu Ala Tyr Arg Tyr Ala Asp Leu Leu Ala Lys Val Asn Gly Glu Tyr
            35                  40                  45

Thr Ala Asp Leu Glu Asp Gly Gly Tyr Thr Ile Asn Ile Lys Phe Ala
        50                  55                  60

Gly Lys Glu Gln Pro Gly Glu Asn Pro Gly
65                  70

<210> SEQ ID NO 172
<211> LENGTH: 72
<212> TYPE: PRT
<213> ORGANISM: Peptostreptococcus magnus

<400> SEQUENCE: 172

Pro Lys Glu Glu Val Thr Ile Lys Ala Asn Leu Ile Phe Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Val Asn Gly Glu Tyr
            35                  40                  45

Thr Ala Asp Leu Glu Asp Gly Gly Tyr Thr Ile Asn Ile Lys Phe Ala
        50                  55                  60

Gly Lys Glu Gln Pro Gly Glu Asn
65                  70
```

The invention claimed is:

1. A method for preparation of a separation matrix, comprising the steps of:
   a) providing a solid support and an alkali-stable ligand derived from a bacterial immunoglobulin-binding protein;
   b) reacting said alkali-stable ligand with said solid support to form a separation matrix having covalently coupled alkali-stable ligands; and
   c) washing said separation matrix having covalently coupled alkali-stable ligands with a wash solution comprising at least 10 mM of an alkali metal hydroxide;
      wherein the separation matrix is substantially free from non-covalently coupled ligands derived from said bacterial immunoglobulin-binding protein; and
      wherein said alkali-stable ligand derived from a bacterial immunoglobulin-binding protein is capable of withstanding incubation with 0.1 M NaOH for 100× 10 min at 22+/−2° C. with less than a 45% reduction in binding capacity towards IgG.

2. The method of claim 1, wherein said alkali-stable ligand derived from a bacterial immunoglobulin-binding protein is an alkali-stable Protein A ligand.

3. The method of claim 1, wherein said alkali-stable ligand derived from a bacterial immunoglobulin-binding protein is an alkali-stable Protein L ligand.

4. The method of claim 1, wherein said alkali-stable ligand derived from a bacterial immunoglobulin-binding protein is an alkali-stable Protein G ligand.

5. The method of claim 1, wherein said solid support comprises a plurality of support particles.

6. The method of claim 1, wherein step c) is repeated at least once.

7. The method of claim 1, wherein step c) is repeated at least 5 times.

8. The method of claim 1, further comprising, after step c), a step d) of transferring said separation matrix to a storage solution.

9. The method of claim 8, further comprising, after step d), a step of dispensing said separation matrix into transport containers.

10. The method of claim 1, wherein step c) is performed within 24 h after step b).

11. The method of claim 1, wherein in step c) the wash solution comprises 25 mM-1 M of an alkali metal hydroxide.

12. The method of claim 1, wherein in step c) the wash solution comprises 40 mM-1 M of an alkali metal hydroxide.

13. The method of claim 1, wherein in step c) the wash solution comprises 40 mM-1 M NaOH or KOH.

14. The method of claim 1, wherein in step c) the separation matrix is incubated with the wash solution during 2-60 min.

15. The method of claim 14, wherein, after incubation, the wash solution is removed by filtration.

16. The method of claim 1, wherein in step c) the temperature is 2-40° C.

17. The method of claim 1, further comprising, before step b), a step a') of activating said solid support.

18. The method of claim 17, wherein step a') comprises the formation of aldehyde groups on said solid support.

19. The method of claim 17, wherein step a') comprises the formation of epoxide groups on said solid support.

20. The method of claim 19, wherein after step b), said separation matrix comprises residual epoxide groups.

21. The method of claim 15, wherein the alkali-stable ligand derived from a bacterial immunoglobulin-binding protein comprises lysine residues.

22. The method of claim 19, wherein the alkali-stable ligand derived from a bacterial immunoglobulin-binding protein comprises a cysteine residue with a thiol capable of reacting with said epoxide groups.

23. The method of claim 22, wherein said cysteine residue is proximal to a C-terminus or an N-terminus of said alkali-stable ligand derived from a bacterial immunoglobulin-binding protein.

24. The method of claim 1, wherein said alkali-stable ligand derived from a bacterial immunoglobulin-binding protein is capable of withstanding incubation with 0.5 M NaOH for 100×10 min at 22+/−2° C. with less than 45% reduction in binding capacity towards IgG.

25. The method of claim 1, wherein said alkali-stable ligand derived from a bacterial immunoglobulin-binding protein comprises at least one alkali-stable Protein A domain.

26. The method of claim 1, wherein said alkali-stable ligand derived from a bacterial immunoglobulin-binding protein comprises a multimer of alkali-stable Protein A domains.

27. The method of claim 26, wherein said multimer comprises at least four alkali-stable Protein A domains.

28. The method of claim 26, wherein said multimer comprises at least six alkali-stable Protein A domains.

29. The method of claim 1, wherein said alkali-stable ligand derived from a bacterial immunoglobulin-binding protein comprises at least one alkali-stable Protein L domain.

30. The method of claim 1, wherein said alkali-stable ligand derived from a bacterial immunoglobulin-binding protein comprises a multimer of alkali-stable Protein L domains.

31. The method of claim 1, wherein said alkali-stable ligand derived from a bacterial immunoglobulin-binding protein comprises at least one alkali-stable Protein G domain.

32. The method of claim 1, wherein said alkali-stable ligand derived from a bacterial immunoglobulin-binding protein comprises a multimer of alkali-stable Protein G domains.

33. The method of claim 1, wherein said solid support comprises a crosslinked polysaccharide.

34. The method of claim 1, wherein said solid support comprises crosslinked agar or agarose.

35. The method of claim 1, wherein said separation matrix comprises at least 11 mg covalently bound ligand per mL matrix.

36. The method of claim 1, wherein after step c), said separation matrix produces a ligand leakage of less than 40 ng ligand per mg IgG, as measured by an ELISA assay in an IgG eluate pool.

37. The method of claim 1, which is a method of removing non-covalently bound Protein A ligand from the separation matrix.

38. The method of claim 37, which is a method of removing non-covalently bound Protein A ligand from the separation matrix during preparation of the separation matrix.

39. The method of claim 1, which is a method of preparing a separation matrix comprising covalently coupled alkali-stable Protein A ligands and being substantially free from non-covalently coupled Protein A ligands.

40. The method of claim 1, which is a method of preparing a separation matrix comprising covalently coupled alkali-stable Protein L ligands and being substantially free from non-covalently coupled Protein L ligands.

41. The method of claim 1, which is a method of preparing a separation matrix comprising covalently coupled alkali-stable Protein G ligands and being substantially free from non-covalently coupled Protein G ligands.

42. The method of claim 1, wherein said alkali metal hydroxide comprises NaOH, KOH, or any mixture thereof.

43. The method of claim 1, wherein said solid support comprises a plurality of porous support particles.

44. The method of claim 1, wherein in step c) the wash solution comprises 50-200 mM of an alkali metal hydroxide.

45. The method of claim 1, wherein in step c) the wash solution comprises 50-200 mM NaOH or KOH.

46. The method of claim 1, wherein in step c) the separation matrix is incubated with the wash solution during 5-30 min.

47. The method of claim 1, wherein in step c) the temperature is 20-25° C.

48. The method of claim 1, wherein said separation matrix comprises at least 15 mg covalently bound ligand per mL matrix.

\* \* \* \* \*